US006624185B2

(12) United States Patent
Glombik et al.

(10) Patent No.: US 6,624,185 B2
(45) Date of Patent: Sep. 23, 2003

(54) DIARYLCYCLOALKYL DERIVATIVES, PROCESSES FOR THEIR PREPARATION AND THEIR USE AS PHARMACEUTICALS

(75) Inventors: Heiner Glombik, Hofheim (DE); Eugen Falk, Frankfurt (DE); Wendelin Frick, Hünstetten-Beuerbach (DE); Stefanie Keil, Hofheim (DE); Hans-Ludwig Schäfer, Hochheim (DE); Lothar Schwink, Stadtallendorf (DE); Wolfgang Wendler, Idstein (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 10/231,432

(22) Filed: Aug. 30, 2002

(65) Prior Publication Data

US 2003/0144332 A1 Jul. 31, 2003

(30) Foreign Application Priority Data

Aug. 31, 2001 (DE) .......................... 101 42 734
May 24, 2002 (DE) .......................... 102 23 273

(51) Int. Cl.$^7$ .................. A61K 31/421; A61P 3/10; C07D 236/34
(52) U.S. Cl. ....................... 514/374; 548/236
(58) Field of Search ................. 548/236; 514/374

(56) References Cited

U.S. PATENT DOCUMENTS

| | | | |
|---|---|---|---|
| 3,174,901 A | 3/1965 | Sterne | |
| 5,190,923 A | 3/1993 | Vincent et al. | |
| 5,814,647 A | 9/1998 | Urban et al. | |
| 6,221,633 B1 | 4/2001 | Ertl et al. | |
| 6,221,897 B1 | 4/2001 | Frick et al. | |
| 6,245,744 B1 | 6/2001 | Frick et al. | |
| 6,342,512 B1 | 1/2002 | Kirsch et al. | |
| 6,380,230 B1 | 4/2002 | Brodin et al. | |

FOREIGN PATENT DOCUMENTS

| | | |
|---|---|---|
| EP | 0 462 884 | 12/1991 |
| WO | 97/26265 | 7/1997 |
| WO | 97/28149 | 8/1997 |
| WO | 97/41097 | 11/1997 |
| WO | 98/08871 | 3/1998 |
| WO | 99/03861 | 1/1999 |
| WO | 99/15525 | 4/1999 |
| WO | 00/40569 | 7/2000 |
| WO | 00/63208 | 10/2000 |
| WO | 00/64876 | 11/2000 |
| WO | WO 00/64876 | 11/2000 |
| WO | 00/64888 | 11/2000 |
| WO | 00/66585 | 11/2000 |
| WO | 00/71549 | 11/2000 |
| WO | 00/78312 | 12/2000 |
| WO | 01/09111 | 2/2001 |
| WO | 01/83451 | 11/2001 |
| WO | 01/85695 | 11/2001 |
| WO | 01/91752 | 12/2001 |

OTHER PUBLICATIONS

Beck et al., "The Ontogeny Of Peroxisome–Proliferator–Activated Receptor Gene Expression In The Mouse And Rat," *Proc. R. Soc. Lond. B*, 247:83–87 (1992).
Vidal–Puig et al., "Regulation of PPAR γ Gene Expression By Nutrition And Obesity In Rodents," *J. Clin. Invest.*, 97(11):2553–2561 (1996).
Okada et al., "Synthesis and Antitumor Activities of Prodrugs of Benzoylphenylureas," *Chem. Pharm. Bull.*, 42(1), 57–61 (1994).
Lee et al., "Leptin Agonists as a Potential Approach to the Treatment of Obesity," *Drugs of the Future*, 26(9), 873–881 (2001).
Salvador et al., "Perspectives in the Therapeutic Use of Leptin," *Expert Opin. Pharmacother.*, 2(10), 1615–1622 (2001).
Zunft et al.,"Carob Pulp Preparation for Treatment of Hypercholesterolemia," *Advances in Therapy*, 18(5), 230–236 (2001).
Motojima, "Peroxisome Proliferator–Activated Receptor (PPAR): Structure, Mechanisms of Activation and Diverse Functions," *Cell Structure and Function*, 18, 267–277 (1993).
Tyle, "Iontophoretic Devices for Drug Delivery," *Pharmaceutical Research*, 3(6), 318–326 (1986).
Horikoshi et al., "Troglitazone—A Novel Antidiabetic Drug for Treating Insulin Resistance," *DDT*, 3(2), 79–88 (1998).
Demetri et al., "Induction of Solid Tumor Differentiation by the Peroxisome Proliferator–Activated Receptor–γ Ligand Troglitazone in Patients with Liposarcoma," *Proc. Natl. Acad. Sci. USA*, 96, 3951–3956 (1999).
Elstner et al., "Ligands for Peroxisome Proliferator–Activated Receptor γ and Retinoic Acid Receptor Inhibit Growth and Induce Apoptosis of Human Breast Cancer Cells in vitro and in BNX Mice," *Proc. Natl. Acad. Sci. USA*, 95, 8806–8811 (1998).

(List continued on next page.)

*Primary Examiner*—Robert W. Ramsuer
(74) *Attorney, Agent, or Firm*—Finnegan, Henderson, Farabow, Garrett & Dunner, L.L.P.

(57) ABSTRACT

Diarylcycloalkyl derivatives and their physiologically acceptable salts and physiologically functional derivatives are disclosed. The compounds include those of formula I,

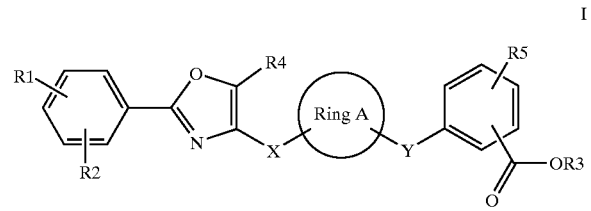

in which the radicals are as defined, and their physiologically acceptable salts and processes for their preparation. The compounds typically have lipid- and/or triglyceride-lowering properties and are suitable, for example, for the treatment of disorders of lipid metabolism, of type II diabetes, and of syndrome X.

23 Claims, No Drawings

OTHER PUBLICATIONS

Sarraf et al., "Differentiation and Reversal of Malignant Changes in Colon Cancer through PPARγ," Nature Medicine, 4(9), 1046–1052 (1998).

Dunaif et al., "The Insulin–Sensitizing Agent Troglitazone Improves Metabolic and Reproductive Abnormalities in the Polycystic Ovary Syndrome," J. Clin. Endocrinol. Metab., 81(9), 3299–3306 (1996).

Löhrke et al., "Detection and Functional Characterisation of the Transcription Factor Peroxisome Proliferator–Activated Receptor γ in Lutein Cells," Journal of Endocrinology, 159, 429–439 (1998).

Poynter et al., "Peroxisome Proliferator–Activated Receptor α Activation Modulates Cellular Redox Status, Represses Nuclear Factor–κβ Signaling, and Reduces Inflammatory Cytokine Production in Aging," J. Biol. Chem., 273(49), 32833–32841 (1998).

Pineda–Torra et al., "Peroxisome Proliferator–Activated Receptor Alpha in Metabolic Disease, Inflammation, Atherosclerosis and Aging," Curr. Opinion in Lipidology, 10, 151–159 (1999).

Colville–Nash et al., "Inhibition of Inducible Nitric Oxide Synthase by Peroxisome Proliferator–Activated Receptor Agonists: Correlation with Induction of Heme Oxygenase 1," Journal of Immunology, 161, 978–984 (1998).

Staels et al., "Activation of Human Aortic Smooth–Muscle Cells is Inhibited by PPARα but not by PPARγ Activators," Nature, 393, 790–793 (1998).

Green, "Receptor–Mediated Mechanisms of Peroxisome Proliferators," Biochemical Pharmacology, 43(3), 393–401 (1992).

Göttlicher et al., "Fatty acids Activate a Chimera of the Clofibric Acid–Activated Receptor and the Glucocorticoid Receptor," Proc. Natl. Acad. Sci. USA, 89, 4653–4657 (1992).

Schoonjans, "Peroxisome Proliferator–Activated Receptors, Orphans with Ligands and Functions," Current Opinion in Lipidology, 8, 159–166 (1997).

Schmidt et al., "Identification of a New Member of the Steroid Hormone Receptor Superfamily that is Activated by a Peroxisome Proliferator and Fatty Acids," Molecular Endocrinology, 6, 1634–1641 (1992).

Amri et al., "Cloning of a Protein That Mediates Transcriptional Effects of Fatty Acids in Preadipocytes," J. Biol. Chem., 270(5), 2367–2371 (1995).

Frick et al., "Prevention of the Angiographic Progression of Coronary and Vein–Graft Atherosclerosis by Gemfibrozil After Coronary Bypass Surgery in Men with Low Levels of HDL Cholesterol," Circulation, 96, 2137–2143 (1997).

De Faire et al., "Retardation of Coronary Atherosclerosis: The Bezafibrate Coronary Atherosclerosis Intervention Trial (BECAIT) and Other Angiographic Trials," Cardiovasc. Drugs Ther., 11, 257–263 (1997).

Lehmann et al., "An Antidiabetic Thiazolidinedione Is a High Affinity Ligand for Peroxisome Proliferator–activated Receptor γ (PPARγ)," J. Biol. Chem., 270(22), 12953–12956 (1995).

Elbrecht et al., "Molecular Cloning, Expression and Characterization of Human Peroxisome Proliferator Activated Receptors γ1 and γ2," BBRC, 224, 431–437 (1996).

Forman et al., "15–Deoxy–$\Delta^{12,\ 14}$–Prostaglandin $J_2$ Is a Ligand for the Adipocyte Determination Factor PPARγ," 83, 803–812 (1995).

Kliewer et al., "A Prostaglandin $J_2$ Metabolite Binds Peroxisome Proliferator–Activated Receptor γ and Promotes Adipocyte Differentiation," Cell, 83, 813–819 (1995).

Staels et al., "Role of PPAR in the Pharmacological Regulation of Lipoprotein Metabolism by Fibrates and Thiazolidinediones," Curr. Pharm. Des., 3(1), 1–14 (1997).

Fruchart et al., "PPARS, Metabolic Disease and Atherosclerosis," Pharmacol. Research, 44(5), 345–352 (2001).

Kersten et al., "Roles of PPARs in Health and Disease," Nature, 405, 421–424 (2000).

Pineda–Torra et al., "Peroxisome Proliferator–Activated Receptors: From Transcriptional Control to Clinical Practice," Curr. Opin. Lipidol., 12, 245–254 (2001).

Asakawa et al., "Cocaine–Amphetamine–Regulated Transcript Influences Energy Metabolism, Anxiety and Gastric Emptying in Mice," Hormone & Metabolic Research, 33, 554–558 (2001).

DIARYLCYCLOALKYL DERIVATIVES, PROCESSES FOR THEIR PREPARATION AND THEIR USE AS PHARMACEUTICALS

CROSS-REFERENCE TO RELATED APPLICATIONS

The present application claims priority under 35 U.S.C. §119 of German Application Nos. 10142734.4 and 10223273.3, filed Aug. 31, 2001 and May 24, 2002, respectively, the disclosures of which are expressly incorporated by reference herein.

DESCRIPTION

1. Field of the Invention

The invention relates to diarylcycloalkyl derivatives and to their physiologically acceptable salts and physiologically functional derivatives.

2. Background of the Invention

Compounds of similar structure have already been described in the prior art for the treatment of hyperlipidemia and diabetes (PCT/US/0011490).

SUMMARY OF THE INVENTION

An object of the invention is to provide compounds having a therapeutically exploitable triglyceride-lowering action and a favorable effect on lipid and carbohydrate metabolism, such as for syndromes of dyslipidemias, type II diabetes and the metabolic syndrome/syndrome X. Another object of the invention is to provide compounds having improved action compared with the compounds of PCT/US00/14490. The compounds of the invention may activate the PPARα receptor.

In one aspect, the present invention is directed to a compound of formula I

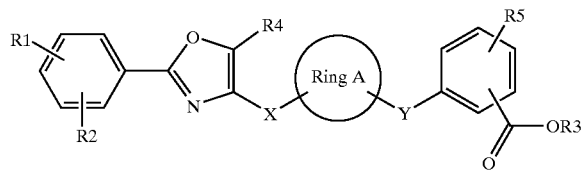

in which
  Ring A is $(C_3-C8)$-cycloalkyl or $(C_3-C_8)$-cycloalkenyl where, in the cycloalkyl or cycloalkenyl rings, one or more carbon atoms may be replaced by oxygen atoms;
  R1, R2, R4, R5 independently of one another are H, F, Cl, Br, OH, NO$_2$, CF$_3$, OCF$_3$, $(C_1-C_6)$-alkyl or O-$(C_1-C_6)$-alkyl;
  R3 is H or $(C_1-C_6)$-alkyl;
  x is $(C_1-C_6)$-alkyl where, in the alkyl group, one or more carbon atoms may be replaced by oxygen atoms;
  Y is $(C_1-C_6)$-alkyl where, in the alkyl group, one or more carbon atoms may be replaced by oxygen atoms;
and its physiologically acceptable salts.

In another aspect, the present invention is directed to a compound of formula Ia

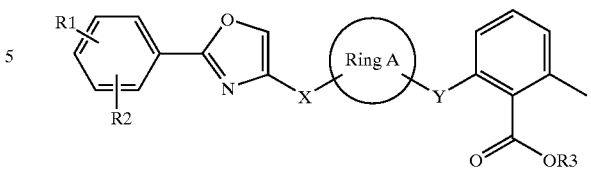

wherein
  Ring A is cyclohexyl;
  R1, R2 independently of one another are H, F, Cl, Br, OH, NO$_2$, CF$_3$, OCF$_3$, $(C_1-C_6)$-alkyl or O-$(C_1-C_6)$-alkyl;
  R3 is H or $(C_1-C_6)$-alkyl;
  X is $(C_1-C_6)$-alkyl where, in the alkyl group, one or more carbon atoms may be replaced by oxygen atoms;
  Y is $(C_1-C_6)$-alkyl where, in the alkyl group, one or more carbon atoms may be replaced by oxygen atoms; and its physiologically acceptable salts.

In another aspect, the present invention is directed to a pharmaceutical, comprising at least one of the above compounds or physiologically acceptable salts and a pharmaceutically acceptable carrier.

In still another aspect, the present invention is directed to a pharmaceutical, comprising at least one of the above compounds or physiologically acceptable salts, at least one further active compound, and a pharmaceutically acceptable carrier.

In yet another aspect, the present invention is directed to a pharmaceutical, comprising at least one of the above compounds or physiologically acceptable salts, at least one lipid- or triglyceride-lowering active compound, and a pharmaceutically acceptable carrier.

The present invention is also directed to a method of treating a lipid metabolism disorder, type II diabetes, syndrome X, disturbed glucose tolerance, eating disorders, obesity, cardiomyopathy, cardiac insufficiency, osteoporosis, atherosclerosis, Alzheimer's disease, or inflammation, comprising administering to a host in need of such treatment an effective amount of at least one the above compounds or physiologically acceptable salts.

In another aspect, the present invention is directed to a method of treating a lipid metabolism disorder, type II diabetes, or syndrome X, comprising administering to a host in need of such treatment an effective amount of a combination of at least one of the above compounds or physiologically acceptable salts and at least one further active compound.

In another aspect, the present invention is directed to a process for preparing a pharmaceutical, comprising mixing at least one of the above compounds or physiologically acceptable salts with a pharmaceutically acceptable carrier to form a mixture and bringing this mixture into a form suitable for administration to form the pharmaceutical.

DESCRIPTION OF THE INVENTION

The particulars shown herein are by way of example and for purposes of illustrative discussion of the various embodiments of the present invention only and are presented in the cause of providing what is believed to be the most useful and readily understood description of the principles and conceptual aspects of the invention. In this regard, no attempt is made to show details of the invention in more detail than is necessary for a fundamental understanding of the invention, the description making apparent to those skilled in the art how the several forms of the invention may be embodied in practice.

Unless otherwise stated, a reference to a compound or component, includes the compound or component by itself, as well as in combination with other compounds or components, such as mixtures of compounds.

The invention relates to compounds of formula I

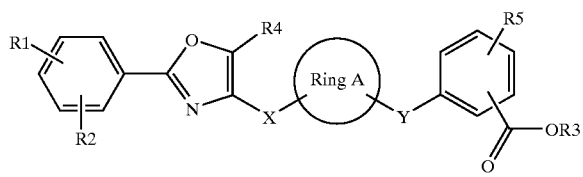

in which

Ring A is $(C_3-C_8)$-cycloalkyl or $(C_3-C_8)$-cycloalkenyl where, in the cycloalkyl or cycloalkenyl rings, one or more carbon atoms may be replaced by oxygen atoms;

R1, R2, R4, R5 independently of one another are H, F, Cl, Br, OH, $NO_2$, $CF_3$, $OCF_3$, $(C_1-C_6)$-alkyl or O-$(C_1-C_6)$-alkyl;

R3 is H or $(C_1-C_6)$-alkyl;

X is $(C_1-C_6)$-alkyl where, in the alkyl group, one or more carbon atoms may be replaced by oxygen atoms;

Y is $(C_1-C_6)$-alkyl where, in the alkyl group, one or more carbon atoms may be replaced by oxygen atoms;

and their physiologically acceptable salts.

The invention also includes compounds of formula I in which

Ring A is $(C_3-C_8)$-cycloalkyl or $(C_3-C_8)$-cycloalkenyl where, in the cycloalkyl or cycloalkenyl rings, one or more carbon atoms may be replaced by oxygen atoms;

R1, R2, R4 independently of one another are H, F, Cl, Br, OH, $NO_2$, CF3, $OCF_3$, $(C_1-C_6)$-alkyl or O-$(C_1-C_6)$-alkyl;

R5 is $(C_1-C_6)$-alkyl;

R3 is H or $(C_1-C_6)$-alkyl;

X is $(C_1-C_6)$-alkyl where, in the alkyl group, one or more carbon atoms may be replaced by oxygen atoms;

Y is $(C_1-C_6)$-alkyl where, in the alkyl group, one or more carbon atoms may be replaced by oxygen atoms;

and their physiologically acceptable salts.

The invention further includes compounds of formula I in which

Ring A is $(C_3-C_8)$-cycloalkyl or $(C_3-C_8)$-cycloalkenyl;

R1, R2 independently of one another are H, F, Cl, Br, OH, $NO_2$, $CF_3$, $OCF_3$, $(C_1-C_6)$-alkyl or O-$(C_1-C_6)$-alkyl;

R3 is H or $(C_1-C_6)$-alkyl;

X is $(C_1-C_6)$-alkyl where, in the alkyl group, one or more carbon atoms may be replaced by oxygen atoms;

Y is $(C_1-C_6)$-alkyl where, in the alkyl group, one or more carbon atoms may be replaced by oxygen atoms;

and their physiologically acceptable salts.

The invention also includes compounds of formula Ia

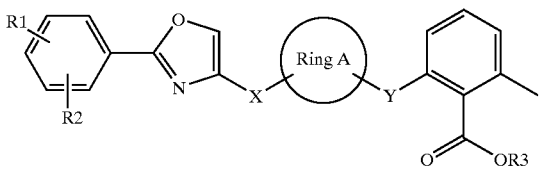

wherein

Ring A is cyclohexyl;

R1, R2 independently of one another are H, F, Cl, Br, OH, $NO_2$, $CF_3$, $OCF_3$, $(C_1-C_6)$-alkyl or O-$(C_1-C_6)$-alkyl;

R3 is H or $(C_1-C_6)$-alkyl;

X is $(C_1-C_6)$-alkyl where, in the alkyl group, one or more carbon atoms may be replaced by oxygen atoms;

Y is $(C_1-C_6)$-alkyl where, in the alkyl group, one or more carbon atoms may be replaced by oxygen atoms;

and their physiologically acceptable salts.

The invention embraces compounds of formula I in the form of their racemates, racemic mixtures and pure enantiomers, and also their diastereomers and mixtures thereof.

The alkyl radicals in the substituents R1, R2, R3, R4 and R5 can be straight-chain or branched.

Pharmaceutically acceptable salts are suitable for medical applications because of their greater solubility in water compared with the starting or base compounds. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acids, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acids. Suitable pharmaceutically acceptable basic salts are ammonium salts, alkali metal salts (such as sodium and potassium salts) and alkaline earth metal salts (such as magnesium and calcium salts).

Salts with a pharmaceutically unacceptable anion such as, for example, trifluoroacetate likewise belong within the scope of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of formula I of the invention, for example, an ester which is able, on administration to a mammal such as, for example, a human, to form (directly or indirectly) a compound of formula I or an active metabolite thereof.

Physiologically functional derivatives also include prodrugs of the compounds of the invention, as described, for example, in H. Okada et al., Chem. Pharm. Bull. 1994, 42, 57–61. Such prodrugs can be metabolized in vivo to a compound of the invention. These prodrugs may themselves have activity or not.

The compounds of the invention may also-exist in various polymorphous forms, for example as amorphous and crystalline polymorphous forms. All polymorphous forms of the compounds of the invention belong within the scope of the invention and are a further aspect of the invention.

All references hereinafter to "compound(s) of formula I" refer to compound(s) of formula I as described above, and to the salts, solvates and physiologically functional derivatives thereof as described herein.

The amount of a compound of formula I necessary to achieve the desired biological effect depends on a number of factors, for example the specific compound chosen, the intended use, the mode of administration and the clinical condition of the patient. The daily dose is generally in the range from about 0.3 mg to 100 mg (typically from about 3 mg to 50 mg) per day and per kilogram of body weight, for example about 3–10 mg/kg/day. An intravenous dose may be, for example, in the range from about 0.3 mg to 1.0 mg/kg, which can suitably be administered as an infusion of about 10 ng to 100 ng per kilogram and per minute. Suitable infusion solutions for these purposes may contain, for example, from about 0.1 ng to 10 mg, typically from about 1 ng to 10 mg, per milliliter. Single doses may contain, for example, from about 1 mg to 10 g of the active compound. Thus, ampoules for injections may contain, for example, from about 1 mg to 100 mg, and single-dose formulations which can be administered orally, such as, for example, capsules or tablets, may contain, for example, from about 1.0 to 1000 mg, typically from about 10 to 600 mg. For the therapy of the abovementioned conditions, the compounds of formula I may be used as the compound itself, but they may be in the form of a pharmaceutical composition with an acceptable carrier. The carrier is acceptable in the sense that it is compatible with the other ingredients of the composition and is not harmful to the patient's health. The carrier may be a solid or a liquid or both and is often formulated with the compound as a single dose, for example as a tablet, which may contain from about 0.05% to 95% by weight of the active compound. Other pharmaceutically active substances may likewise be present, including other compounds of formula 1. The pharmaceutical compositions of the invention can be produced by one of the known pharmaceutical methods, which may essentially consist of mixing the ingredients with pharmacologically acceptable carriers and/or excipients.

Pharmaceutical compositions of the invention include those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units such as, for example, capsules, wafers, suckable tablets or tablets, each of which contain a defined amount of the compound of formula l; as powders or granules, as solution or suspension in an aqueous or nonaqueous liquid; or as an oil-in-water or water-in-oil emulsion. These compositions may, as already mentioned, be prepared by any suitable pharmaceutical method which includes a step in which the active compound and the carrier (which may consist of one or more additional ingredients) are brought into contact. The compositions are generally produced by uniform and homogeneous mixing of the active compound with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one or more surface-active/dispersing agent(s) in a suitable machine. Molded tablets can be produced by molding the compound which is in powder form and is moistened with an inert liquid diluent in a suitable machine.

Pharmaceutical compositions which are suitable for peroral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

The pharmaceutical compositions suitable for parenteral administration may comprise sterile aqueous preparations of a compound of formula I, which may be isotonic with the blood of the intended recipient. These preparations may be administered intravenously, although administration may also take place by subcutaneous, intramuscular or intradermal injection. These preparations can be produced by mixing the compound with water and making the resulting solution sterile and isotonic with blood. Injectable compositions of the invention generally contain from about 0.1 to 5% by weight of the active compound.

Pharmaceutical compositions suitable for rectal administration may be in the form of single-dose suppositories. These can be produced by mixing a compound of formula I with one or more conventional solid carriers, for example cocoa butter, and shaping the resulting mixture.

Pharmaceutical compositions suitable for topical use on the skin may be in the form of an ointment, cream, lotion, paste, spray, aerosol or oil. Carriers which can be used are petrolatum, lanolin, polyethylene glycols, alcohols and combinations of two or more of these substances. The active compound is generally present in a concentration of from about 0.1 to 15% by weight of the composition, for example from about 0.5 to 2%.

Transdermal administration is also possible. Pharmaceutical compositions suitable for transdermal uses can be in the form of single plasters which are suitable for long-term close contact with the patient's epidermis. Such plasters suitably contain the active compound in an aqueous solution which is buffered where appropriate, dissolved and/or dispersed in an adhesive or dispersed in a polymer. A suitable active compound concentration is about 1% to 35% by weight, or about 3% to 15%. A possibility is for the active compound to be released by electrotransport or iontophoresis as described, for example, in Pharmaceutical Research, 2(6): 318 (1986).

The invention furthermore provides a process for preparing the compounds of formula I which comprises obtaining the compounds of formula I by proceeding in accordance with the reaction scheme below:

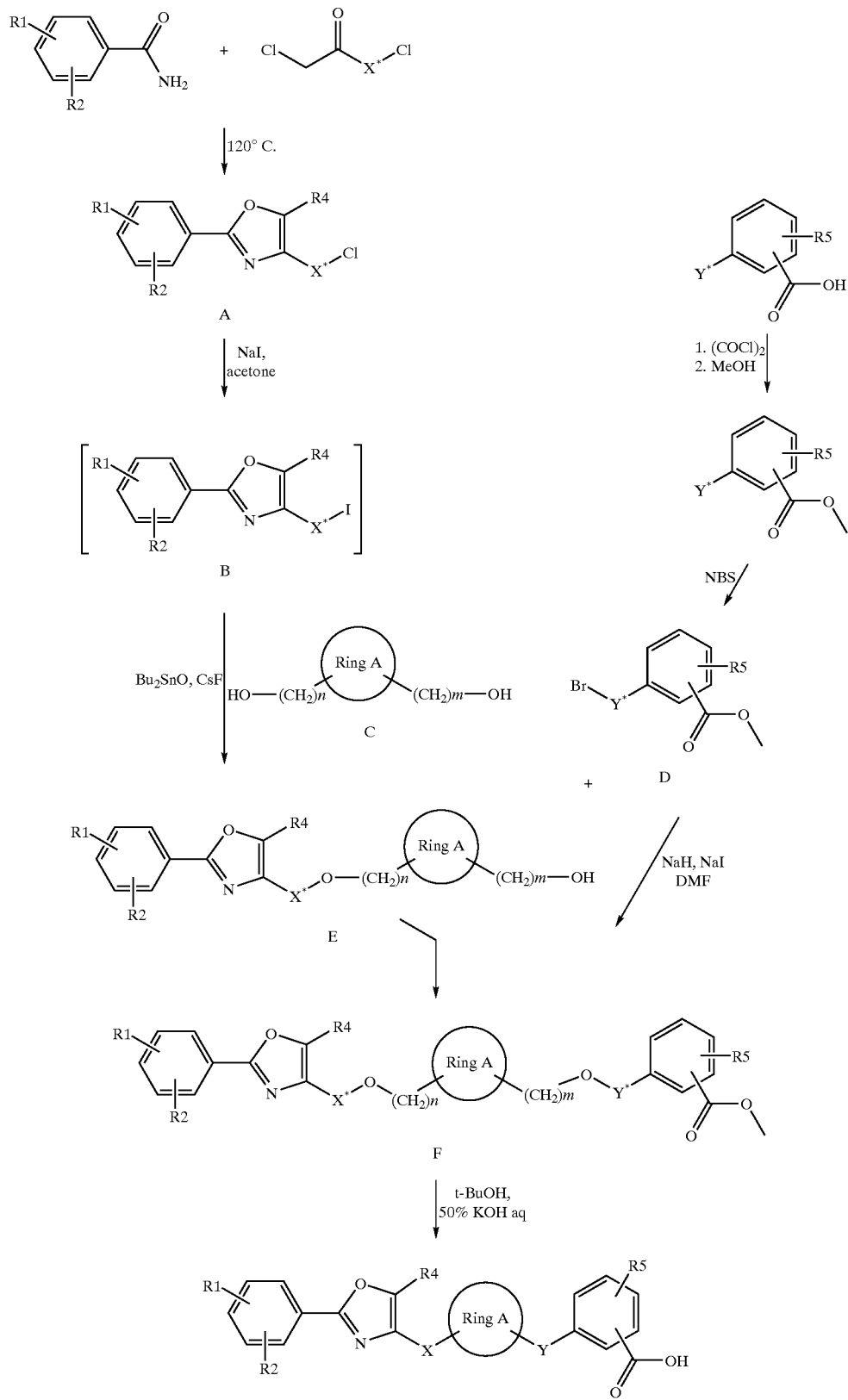

To this end, compounds of formula A in which R1, R2, R4 and X have the meanings given above are reacted with NaI in acetone with heating at reflux for about 12 to 24 hours, giving a compound of formula B.

The compound of formula B is reacted with a compound of formula C in which n and m are each 0–5, giving a compound of formula E in which R1, R2, R4, m, n and X have the meanings described above. Here, (a) C is deprotonated at room temperature in an inert solvent such as dimethylformamide or tetrahydrofuran using sodium hydride and the n reacted at about 70° C. with the halide, or (b) component C is initially heated with dibutyltin oxide in toluene on a water separator for a number of hours and then, with addition of dimethylformamide, cesium fluoride and iodide B, converted into E by stirring at room temperature for a number of hours, such as between about 10 and 14 hours, preferably overnight.

The compound of formula E is, using a compound of formula D in which Y is as described above, converted into a compound of formula F in which R1, R2, R4, R5, X and Y have the meanings described above. To form an ether bond, E is deprotonated, for example in a mixture of dimethylformamide and tetrahydrofuran using a strong base such as Na hydride at room temperature, and then alkylated with a component D, often with addition of Na iodide.

The compound of formula F is converted into compounds of formula I by hydrolyzing the ester function, for example by heating with potassium hydroxide in an alcohol (ethanol, tert-butanol) and releasing the carboxylic acid group of formula I by acidification. This carboxylic acid group can be derivatized by customary methods to a group of the formula —(C=O)—OR3, where R3 has the meaning described above.

The compounds of formula I act favorably on metabolic disorders. They have a positive effect on lipid and sugar metabolism and, in particular, reduce the concentration of triglycerides and they are suitable for preventing and treating type II diabetes and arteriosclerosis.

The compounds can be administered alone or in combination with one or more further pharmacologically active substances which, for example, act favorably on metabolic disorders and are selected, for example, from antidiabetics, antiadipose agents, antihypertensives and active compounds for treating and/or preventing complications caused by or associated with diabetes.

Suitable further pharmacologically active substances are:

All antidiabetics mentioned in chapter 12 of Rote Liste 2001. They may be combined with the compounds of formula I according to the invention for synergistic improvement of the effect. Administration of the active compound combination may take place either by separate administration of the active compounds to the patients or in the form of combination products in which a plurality of active compounds are present in one pharmaceutical preparation. Most of the active compounds listed below are disclosed in USP Dictionary of USAN and International Drug Names, US Pharmacopeia, Rockville, Md. 2001.

Antidiabetics include insulin and insulin derivatives such as, for example, Lantus® (see www.lantus.com) or HMR 1964, fast-acting insulins (see U.S. Pat. No. 6,221,633), GLP-1 derivatives such as, for example, those disclosed in WO 98/08871 of Novo Nordisk A/S, and orally active hypoglycemic active compounds.

Orally active hypoglycemic active compounds include sulfonylureas, biguanides, meglitinides, oxadiazolidinediones, thiazolidinediones, glucosidase inhibitors, glucagon antagonists, GLP-1 agonists, potassium channel openers such as, for example, those disclosed in WO 97/26265 and WO 99/03861 of Novo Nordisk ANS, insulin sensitizers, inhibitors of liver enzymes involved in the stimulation of gluconeogenesis and/or glycogenolysis, modulators of glucose uptake, compounds which alter lipid metabolism, such as antihyperlipidemic active compounds and antilipidemic active compounds, compounds which reduce food intake, PPAR and PXR agonists and active compounds which act on the ATP-dependent potassium channel of beta cells.

In one embodiment of the invention, the compounds of formula I are administered in combination with an HMG-CoA reductase inhibitor such as simvastatin, fluvastatin, pravastatin, lovastatin, atorvastatin, cerivastatin or rosuvastatin.

In one embodiment of the invention, the compounds of formula I are administered in combination with a cholesterol absorption inhibitor such as, for example, ezetimibe, tiqueside or pamaqueside.

In one embodiment of the invention, the compounds of formula I are administered in combination with a PPAR gamma agonist such as, for example, rosiglitazone, pioglitazone, JTT-501 or GI 262570.

In one embodiment of the invention, the compounds of formula I are administered in combination with a PPAR alpha agonist such as, for example, GW 9578 or GW 7647.

In one embodiment of the invention, the compounds of formula I are administered in combination with a mixed PPAR alpha/gamma agonist such as, for example, GW 1536, AVE 8042, AVE 8134, or AVE 0847, or as described in PCT/US00/11833, PCT/US00/11490, or DE 10142734.4.

In one embodiment of the invention, the compounds of formula I are administered in combination with a fibrate such as, for example, fenofibrate, clofibrate or bezafibrate.

In one embodiment of the invention, the compounds of formula I are administered in combination with an MTP inhibitor such as, for example, implitapide, BMS-201038 or R-103757.

In one embodiment of the invention, the compounds of formula I are administered in combination with a bile acid adsorption inhibitor (see, for example, U.S. Pat. No. 6,245, 744 or U.S. Pat. No. 6,221,897) such as, for example, HMR 1741.

In one embodiment of the invention, the compounds of formula I are administered in combination with a CETP inhibitor such as, for example, JTT-705.

In one embodiment of the invention, the compounds of formula I are administered in combination with a polymeric bile acid adsorbent such as, for example, cholestyramine or colesevelam.

In one embodiment of the invention, the compounds of formula I are administered in combination with an LDL receptor inducer (see U.S. Pat. No. 6,342,512) such as, for example, HMR1171 or HMR 1586.

In one embodiment of the invention, the compounds of formula I are administered in combination with an ACAT inhibitor such as, for example, avasimibe.

In one embodiment of the invention, the compounds of formula I are administered in combination with an antioxidant such as, for example, OPC-14117.

In one embodiment of the invention, the compounds of formula I are administered in combination with a lipoprotein lipase inhibitor such as, for example, NO-1886.

In one embodiment of the invention, the compounds of formula I are administered in combination with an ATP citrate lyase inhibitor such as, for example, SB-204990.

In one embodiment of the invention, the compounds of formula I are administered in combination with a squalene synthetase inhibitor such as, for example, BMS-188494.

In one embodiment of the invention, the compounds of formula I are administered in combination with a lipoprotein (a) lowering agent / HDL enhancer such as, for example, Cl-1027 or nicotinic acid.

In one embodiment of the invention, the compounds of formula I are administered in combination with a lipase inhibitor such as, for example, orlistat.

In one embodiment of the invention, the compounds of formula I are administered in combination with insulin.

In one embodiment, the compounds of formula I are administered in combination with a sulfonylurea such as, for example, tolbutamide, glibenclamide, glipizide or glimepiride.

In one embodiment, the compounds of formula I are administered in combination with a biguanide such as, for example, mefformin.

In another embodiment, the compounds of formula I are administered in combination with a meglitinide such as, for example, repaglinide.

In one embodiment, the compounds of formula I are administered in combination with a thiazolidinedione such as, for example, troglitazone, ciglitazone, pioglitazone, rosiglitazone or the compounds disclosed in WO 97/41097 of Dr. Reddy's Research Foundation, such as 5-[[4-[(3,4-dihydro-3-methyl-4-oxo-2-quinazolinylmethoxy]phenyl] methyl]-2,4-thiazolidinedione.

In one embodiment, the compounds of formula I are administered in combination with an α-glucosidase inhibitor such as, for example, miglitol or acarbose.

In one embodiment, the compounds of formula I are administered in combination with an active compound which acts on the ATP-dependent potassium channel of beta cells, such as, for example, tolbutamide, glibenclamide, glipizide, glimepiride or repaglinide.

In one embodiment, the compounds of formula I are administered in combination with more than one of the aforementioned compounds, for example in combination with a sulfonylurea and metformin, a sulfonylurea and acarbose, repaglinide and metformin, insulin and a sulfonylurea, insulin and metformin, insulin and troglitazone, insulin and lovastatin, etc.

In a further embodiment, the compounds of formula I are administered in combination with CART modulators (see. "Cocaine-amphetamine-regulated transcript influences energy metabolism, anxiety and gastric emptying in mice" Asakawa, A, et al., Hormone and Metabolic Research (2001), 33(9), 554–558), NPY antagonists (for example N-{4-[(4-aminoquinazolin-2-ylamino)methyl] cyclohexylmethyl}-naphthalene-1-sulfonamide hydrochloride (CGP 71683A)), MC4 agonists (for example N-[2-(3a-benzyl-2-methyl-3-oxo-2,3,3a,4,6,7-hexahydropyrazoio[4,3-c]pyridin-5-yl)-1-(4-chlorophenyl)-2-oxoethyl]-1-amino-1,2,3,4-tetrahydronaphthalene-2-carboxamide (WO 01/91752)), orexin antagonists (for example 1-(2-methylbenzoxazol-6-yl)-3-[1,5]naphthyridin-4-ylurea hydrochloride (SB-334867-A)), H3 agonists (for example 3-cyclohexyl-1-(4,4, dimethyl-1,4,6,7-tetrahydroimidazo[4,5-c]pyridin-5-yl)propan-1-one oxalic acid salt (WO 00/63208)); TNF agonists, CRF antagonists (for example [2-methyl-9-(2,4,6-trimethylphenyl)-9H-1,3,9-triazafluoren [4-yl]dipropylamine (WO 00/66585)), CRF BP antagonists (for example urocortin), urocortin agonists, β3 agonists (for example 1-(4-chloro-3-methanesulfonylmethylphenyl)-2-[2-(2,3-dimethyl-1H-indol-6-yloxy)ethylamino]ethanol hydrochloride (WO 01/83451)), MSH (melanocyte-stimulating hormone) agonists, CCK-A agonists (for example {2-[4-(4-chloro-2,5-dimethoxyphenyl)-5-(2-cyclohexylethyl)-thiazol-2-ylcarbamoyl]-5,7-dimethylindol-1-yl}acetic acid trifluoroacetic acid salt (WO 99/15525)); serotonin reuptake inhibitors (for example dexfenfluramine), mixed serotoninergic and noradrenergic compounds (for example WO 00/71549), 5HT agonists (for example 1-(3-ethylbenzofuran-7-yl)piperazine oxalic acid salt (WO 01/09111)), bombesin agonists, galanin antagonists, growth hormone (for example human growth hormone), growth-hormone-releasing compounds (tert-butyl 6-benzyloxy-1-(2-diisopropylaminoethylcarbamoyl)-3,4-dihydro-1 H-isoquinoline-2-carboxylate (WO 01/85695)), TRH agonists (see, for example, EP 0 462 884), decoupling protein 2 or 3 modulators, leptin agonists (see, for example, Lee, Daniel W.; Leinung, Matthew C.; Rozhavskaya-Arena, Marina; Grasso, Patricia, "Leptin agonists as a potential approach to the treatment of obesity," Drugs of the Future (2001), 26(9), 873–881), DA agonists (for example bromocriptin or doprexin), lipase/amylase inhibitors (for example WO 00/40569), PPAR modulators (for example WO 00/78312), RXR modulators or TR β agonists.

In one embodiment of the invention, the other active compound is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615–1622.

In one embodiment, the other active compound is dex-amphetamine or amphetamine.

In one embodiment, the other active compound is fenfluramine or dexfenfluramine.

In a further embodiment, the other active compound is sibutramine.

In one embodiment, the other active compound is orlistat.

In one embodiment, the other active compound is mazindol or phentermine.

In one embodiment, the compounds of formula I are administered in combination with dietary fiber materials, such as insoluble dietary fiber materials (see, for example, carob/Caromax® (Zunft H J; et al., Carob pulp preparation for treatment of hypercholesterolemia, ADVANCES IN THERAPY (2001 Sep.–Oct.), 18(5), 230–6). Caromax® is a carob-containing product from Nutrinova, Nutrition Specialties & Food Ingredients GmbH, Industriepark Höchst, 65926 Frankfurt/Main, Germany. Combination with Caromax® is possible in one preparation or by separate administration of compounds of formula I and Caromax®. Caromax® can moreover be administered in the form of foodstuffs such as, for example, in bakery products or muesli bars.

It is self-evident that any suitable combination of the compounds of the invention with one or more of the aforementioned compounds and optionally one or more other pharmacologically active substances is regarded as falling within the protection conferred by the present invention.

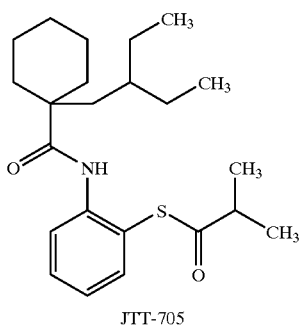

JTT-705

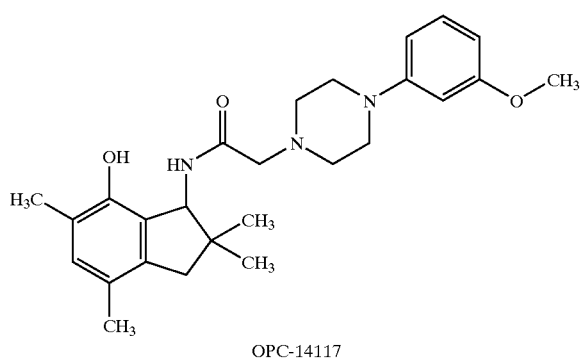

OPC-14117

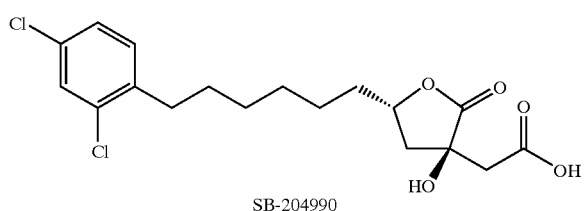

SB-204990

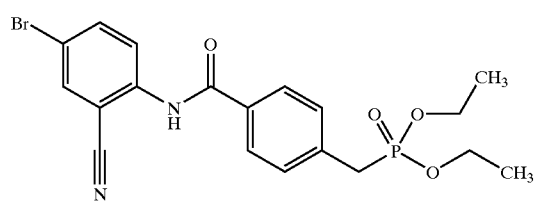

NO-1886

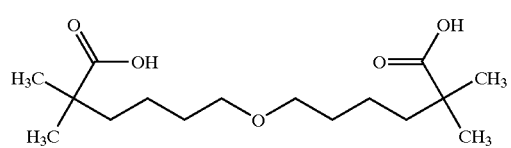

CI-1027

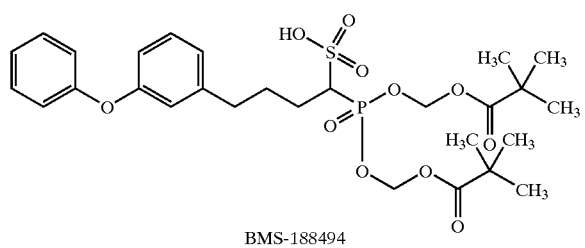

BMS-188494

-continued

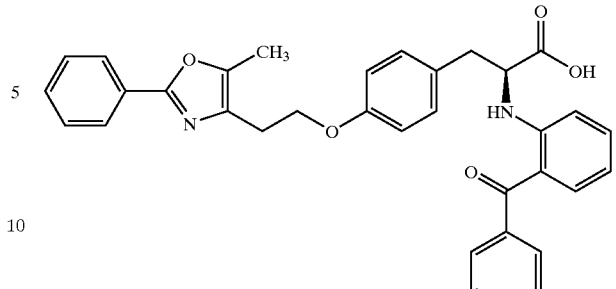

GI 262570

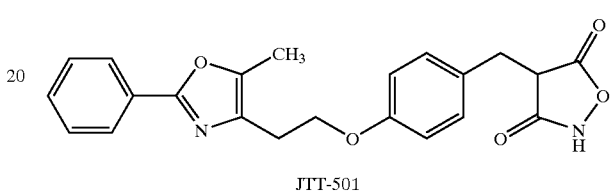

JTT-501

This invention furthermore relates to the use of compounds of formula I and their pharmaceutical compositions as PPAR ligand receptor binders. The PPAR ligand receptor binders according to the invention are suitable for use as agonists or antagonists of the PPAR receptor.

Peroxisome-proliferator-activated receptors (PPAR) can be divided into the three subtypes PPARα, PPARδ and PPAR$_Y$. These are encoded by different genes (Motojima, Cell Structure and Function, 18:267–277, 1993). In addition, there are two isotopes of PPAR$_Y$, PPAR$_{Y1}$ and $_{Y2}$. These two proteins differ in the 30 NH$_2$-terminal amino acids and are the result of an alternative use of promoters and different mRNA splicing (Vidal-Puig, Jiminez, Linan, Lowell, Hamann, Hu, Spiegelman, Flier, Moller, J. Clin. Invest., 97:2553–2561, 1996).

PPAR-modulated biological processes are processes modulated by receptors or combinations of receptors which react to the PPAR receptor ligands described in the present document. These processes include, for example, plasma lipid transport and fatty acid catabolism, regulation of insulin sensitivity and blood glucose levels involved in hypoglycemia/hyperinsulinism (caused, for example, by functional disorders of the pancrease beta-cells, insulin-secreting tumors and/or autoimmune hypoglycemia owing to autoantibodies against insulin, the insulin receptor or autoantibodies having a stimulating action on pancrease beta-cells), macrophage differentiation resulting in the formation of atherosclerotic plaques, in inflammable reactions, carcinogenesis, hyperplasia or adipocyte differentiation.

Adiposity is an excessive buildup of fatty tissue. Recent investigations in this field have shown that PPAR$_Y$ plays a central role in gene expression and differentiation of adipocytes. Excess fatty tissue is associated with the development of serious disorders such as, for example, non-insulin-dependent diabetes mellitus (NIDDM), hypertension, disorders of the coronary arteries, hyperlipidemia, adiposity and certain malignant syndromes. The adipocytes can, by forming tumor necrosis factor a (TNFα) and other molecules, also have an effect on glucose homeostasis.

Non-insulin-dependent diabetes mellitus (NIDDM) or type II diabetes is the more frequent form of diabetes. About 90–95% of hyperglycemia patients suffer from this form of the disease. What is present in NIDDM is apparently a reduction of the mass of the beta cells of the pancreas, a number of different disorders of insulin secretion or reduced insulin sensitivity of the tissue. The symptoms of this form of diabetes include tiredness, frequent urination, thirst, blurred vision, frequent infections and slow healing of wounds, diabetic nerve damage and kidney diseases.

Resistance against the metabolic effects of insulin is one of the main features of non-insulin-dependent diabetes (NIDDM). Insulin resistance is characterized by reduced uptake and conversion of glucose in insulin-sensitive target organs such as, for example, adipocytes and skeletal muscles, and by reduced inhibition of hepatic gluconeogenesis. Functional insulin deficiency and the absent suppression of hepatic gluconeogenesis by insulin leads to hyperglycemia in the fasting state. The pancreas beta-cells compensate for insulin resistance by increased secretion of insulin. However, the beta-cells are not able to maintain this high insulin output, so that the glucose-induced insulin secretion decreases, resulting in a deterioration of glucose homeostasis and finally in the development of manifest diabetes.

Hyperinsulinemia is likewise associated with insulin resistance, hypertriglyceridemia and increased plasma concentrations of low-density lipoproteins. Insulin resistance and hyperinsulinemia combined with these metabolic disorders is called "syndrome X" and is strongly associated with an increased risk of hypertension and disorders of the coronary arteries.

Metformin is known to the person skilled in the art as an agent for treating diabetes in humans (U.S. Pat. No. 3,174,901). The primary action of metformin is reduced formation of glucose in the liver. As is known, Troglitazone® acts primarily by improving the ability of skeletal muscles to react to insulin and to take up glucose. It is known that a combination therapy of metformin and Troglitazone® can be used for treating diabetes-associated disorders (DDT 3:79–88, 1998).

It has been observed that $PPAR_Y$ activators, such as Troglitazone®, convert cancerous tissue in liposarcoma (fat tumors) into normal cells (PNAS 96:3951–3956, 1999). Furthermore, it has been proposed that $PPAR_Y$ activators may be of benefit in the treatment of breast cancer and intestinal cancer (PNAS 95:8806–8811,1998; Nature Medicine 4:1046–1052, 1998).

In addition, $PPAR_Y$ activators such as, for example, Troglitazone® have also been used for treating polycystic ovarial syndrome (PCO). This syndrome, which occurs in women, is characterized by chronic anovulation and hyperandrogenism. Women with this syndrome frequently also suffer from insulin resistance and an increased risk of developing non-insulin-dependent diabetes mellitus (Dunaif, Scott, Finegood, Quintana, Whitcomb, J. Clin. Endocrinol. Metab., 81:3299, 1996).

Furthermore, it has recently been discovered that $PPAR_Y$ activators increase the formation of progesterone and inhibit steroid genesis in granulosa cell cultures and may therefore be suitable for treating climacterium -(U.S. Pat. No. 5,814,647, Urban etal., Sep. 29, 1998; B. Lorke et al., Journal of Endocrinology, 159, 429–39, 1998). Climacterium is defined as the syndrome of the endocrine, somatic and psychological changes which occur in women at the end of the reproductive phase.

Peroxisomes are cellular organelles involved in the control of the redox potential and oxidative stress in cells by metabolizing a large number of substrates such as, for example, hydrogen peroxide. A number of disorders are associated with oxidative stress. Thus, for example, inflammable reactions to tissue damage, pathogenesis of emphysema, ischemia-associated organ damage (shock), doxorubicin-induced heart damage, drug-induced hepatotoxicity, atherosclerosis and lung damage caused by hyperoxia are in each case associated with the formation of reactive oxygen species and changes of the reductive capability of the cell. Accordingly, it has been proposed that $PPAR\alpha$ activators regulate inter alia the redox potential and the oxidative stress in cells and may be useful for treating these disorders (Poynter et al., J. Biol. Chem. 273, 3283341, 1998).

It has also been found that $PPAR\alpha$ agonists inhibit $NF_KB$-mediated transcription and thus modulate various inflammatory reactions, such as, for example, the enzyme paths of inducible nitrous oxide synthase (NOS) and cyclooxygenase-2 (COX-2) (Pineda-Torra, 1. et al., 1999, Curr. Opinion in Lipidology, 10, 151–9) and can therefore be used for therapeutic interventions in a large number of different inflammatory diseases and other pathological conditions (Colville-Nash et al., Journal of Immunology, 161, 978–84, 1998; Staels et al, Nature, 393, 790–3, 1998).

Peroxisome proliferators activate PPAR which, in turn, act as transcription factors and cause differentiation, cell growth and proliferation of peroxisomes. It is also presumed that PPAR activators play a role in hyperplasia and carcinogenesis and change the enzymatic properties of animal cells such as, for example, rodent cells; however, these PPAR activators appear to have only minimal negative effects on human cells (Green, Biochem. Pharm. 43(3):393, 1992). Activation of PPAR leads to a rapid increase of gamma-glutamyl transpeptidase and -catalase.

$PPAR\alpha$ is activated by a number of medium-chain fatty acids and long-chain fatty acids and is involved in the stimulation of 3-oxidation of fatty acids in tissues such as liver, heart, skeletal muscle and brown fatty tissue (Issemann and Green, ibid.; Beck et al., Proc. R. Soc. Lond. 247:83–87, 1992; Gottlicher et al., Proc. Natl. Acad. Sci. USA 89:4653–4657, 1992).

Pharmacological $PPAR\alpha$ activators such as, for example, fenofibrate, clofibrate, gemfibrozil and bezafibrate are likewise involved in the considerable reduction of plasma triglycerides and a moderate reduction of LDL cholesterol, and they are used for treating hypertriglyceridemia, hyperlipidemia and adiposity. It is known that $PPAR\alpha$ is also involved in inflammatory disorders (Schoonjans, K., Current Opinion in Lipidology, 8, 159–66, 1997).

The human nuclear receptor $PPAR\delta$ has been cloned from a cDNA library of human osteosarcoma cells and is described completely in A. Schmidt et al., Molecular Endocrinology, 6:1634–1641 (1992). The contents of this article are hereby incorporated by reference into the present document. It may be pointed out that in the literature $PPAR\delta$ is also referred to as $PPAR\beta$ and as NUC1, but all of these names refer to the same receptor. Thus, in A. Schmidt et al., Molecular Endocrinology, 6:1634–1641,1992, for example, the receptor is referred to as NUC1. $PPAR\delta$ is found both in embryonal and in adult tissue. It has been reported that this receptor is involved in the regulation of the expression of some fat-specific genes and therefore plays a role in the process of adipogenesis (Amri, E. et al., J. Biol. Chem. 270, 2367–71,1995).

It is known that atherosclerotic disorders are caused by a number of factors such as, for example, hypertension, diabetes, low concentrations of high-density lipoproteins (HDL) and high concentrations of low-density lipoproteins (LDL). In addition to reducing the risks by acting on the concentration of the plasma lipids and other risk factors, PPARα agonists have direct atheroprotective actions (Frick, M. H. et al., 1997, Circulation 96:2137–2143, de Faire et al., 1997, Cardiovasc. Drugs Ther. 11 Suppl. 1:257–63).

It has recently been found that PPARδ agonists are useful for increasing HDL level and are therefore suitable for treating atherosclerotic disorders (Leibowitz et al., WO 97/28149). Atherosclerotic disorders include vascular disorders, coronary heart disease, cerebrovascular disorders and disorders of the peripheral vessels. Coronary heart disease includes death by coronary heart disease, myocardial infarction and coronary revascularization. Cerebrovascular diseases include ischemic and hemorrhagic infarcts and transient ischemic attacks.

PPAR$_Y$ subtypes are involved in the activation of adipocyte differentiation and do not play any role in the stimulation of peroxysome proliferation in the liver. Activation of PPAR$_Y$ contributes to adipocyte differentiation by activating the adipocyte-specific gene expression (Lehmann, Moore, Smith-Oliver, Wilkison, Willson, Kliewer, J. Biol. Chem., 270:12953–12956,1995). The DNA sequences of the PPAR$_Y$ subtypes are described in Elbrecht et al., BBRC 224; 431–437 (1996). Although peroxysome proliferators including fibrates and fatty acids activate the transciptory activity of PPARs, only prostaglandin $J_2$ derivatives such as the arachidonic metabolite 15-deoxy-delta$^{12}$, 14-prostaglandin $J_2$ (15d-PGJ$_2$) have been identified as natural ligands specific for the PPAR$_Y$ subtype which also binds to thiazolidinediones. This prostaglandin activates PPAR$_Y$-dependent adipogenesis, but activates PPARα only at high concentrations (Formann, Tontonoz, Chen, Brun, Spiegelman, Evans, Cell, 83:803–812, 1995; Kliewer, Lenhard, Wilson, Patel, Morris, Lehmann, Cell, 83:813–819, 1995). This is a further indication that the subtypes of the PPAR family differ in their pharmacological reaction to ligands.

From this, it can be concluded that compounds which activate PPARα or both PPARα and PPAR$_Y$ have to be effective hypotriglyceridemic drugs which can be used for treating atherosclerosis-associated dislipidemia, non-insulin-dependent diabetes mellitus, syndrome X (Staels, B. et al., Curr. Pharm. Des., 3 (1),1–4 (1997)) and familial combined hyperlipidemia (FCH). Syndrome X is characterized by a first insulin-resistant stage which causes hyperinsulinemia, dyslipidemia and reduced glucose tolerance and which can progress to non-insulin-dependent diabetes mellitus (type II diabetes) characterized by hyperglycemia. FCH is characterized by hypercholesterolemia and hypertriglyceridemia in the same patient and in the'same family.

The present invention relates to compounds of formula I suitable for modulating PPAR receptors, and for a number of other related pharmaceutical applications.

The compounds of formula I are suitable for treating dyslipidemia, insulin resistance, type I and type II diabetes, disturbed glucose tolerance, syndrome X, obesity, eating disorders, thromboses, inflammations, cardiomyopathy and for protecting beta-cells and protection against fatty acid oxidation (see, for example, Jean-Charles Fruchart, Bart Staels and Patrick Duriez: PPARS, Metabolic Disease and Atherosclerosis, Pharmacological Research, Vol. 44, No. 5, 2001; Sander Kersten, Beatrice Desvergne & Walter Wahli: Roles of PPARs in health and disease, NATURE, VOL 405, MAY 25, 2000; Ines Pineda Torra, Giulia Chinetti, Caroline Duval, Jean-Charles Fruchart and Bart Staels: Peroxisome proliferator-activated receptors: from transcriptional control to clinical practice, Curr Opin Lipidol 12: 2001, 245–254).

The activity of the compounds was tested as follows:

To analyze the effectiveness of substances which bind to human PPARα, activating it in agonistic manner, a stable transfected HEK cell line (HEK=human embryo kidney) designated here as "PPARα reporter cell line" is used.

The activity of PPARα agonists is determined in a three-day test, described below:

Day 1

The PPARα reporter cell line is cultivated up to 80% confluence in DMEM medium (#41965–039, Life Technologies) with the following additives: 10% cs-FCS (fetal calf serum, #SH-30068.03, Hyclone), antibiotics (0.5 mg/ml of zeozin [#R250-01, Invitrogen], 0.5 mg/ml of G418 [#10131-019, Life Technologies], 1% penicillin streptomycin solution [#15140-031, Life Technologies]) and 2 mM of L-glutamine (#25030-032, Life Technologies). Cultivation is carried out in standard cell culture bottles (#33111, Becton Dickinson) in a cell culture incubator at 37° C. and 5% $CO_2$. The 80% confluent cells are washed once with 30 ml of PBS (#141-090- 094, Life Technologies), treated with 2 ml of trypsin solution (#25300-054, Life Technologies) at 37° C. for 2 min, taken up in 5 ml of the medium described above and counted in a cell counter. After dilution to 500,000 cells/ml, in each case 100,000 cells are sown into each well of a 96-well microtiter plate having a clear plastic bottom (#3610, Corning Costar). The plates are incubated in a cell incubator at 37° C. and 5% $CO_2$ for 24 h.

Day 2

The PPARα agonists to be tested are dissolved in DMSO at a concentration of 10 mM. This stock solution is diluted in Phenol-Red-free DMEM medium (#21063-029, Life Technologies) to which 5% of cs-FCS (#SH-30068.03, Hyclone), 2 mM of L-glutamine (#25030-032, Life Technologies) and the antibiotics described above (zeozin, G418, penicillin and streptomycin) had been added.

Test substances are usually tested at 11 different concentrations (10 μM; 3.3 μM; 1 μM; 0.33 μM; 0,1 μM; 0.033 μM; 0.01 μM; 0.0033 μM; 0.001 μM; 0.00033 μM and 0.0001 μM). More potent compounds are tested in concentration ranges of from 1 μM to 10 pM or 100 nM to 1 pM. From each well, the medium of the PPARα reporter cell line sown on day 1 is completely removed by aspiration, and immediately, the test substances diluted in medium are added to the cells. Dilution and addition of the substances can be carried out using a robot (Beckman Biomek 2000). The end volume of the test substances diluted in medium is 100 μl per well of a 96-well plate. The DMSO concentration in the assay is always below 0.1% v/v to prevent cytotoxic effects of the solvent.

To demonstrate that the assay is working in each individual plate, a standard PPARα agonist, which is also diluted to 11 different concentrations, is added to each plate. The test plates are incubated in an incubator at 37° C. and 5% $CO_2$ for 24 h.

Day 3

The PPARα receptor cells treated with the test substances are removed from the incubator and frozen at −20° C. for 1 h to improve cell lysis. After the plates have thawed (thawing at room temperature for at least 30 min), 50 μl of buffer 1 (Luc-Screen kit #LS1000, PE Biosystems Tropix) are pipetted into each well and the plates are then transferred into an apparatus for measuring luminescence, fitted with a pipetting unit (Luminoscan Ascent, LabSystems). The luciferase reaction in the measurement apparatus is started by pipetting 50 μl of buffer 2 (Luc-Screen kit #LS1000, PE Biosystems Tropix) into each well of the 96-well plate. Addition of buffer to the individual wells is carried out in defined and identical time intervals following the instructions of the manufacturer (LabSystems). All samples are measured exactly 16 min after addition of buffer 2. Measurement time is 10 sec per sample.

The crude data of the apparatus for measuring luminescence are exported into a Microsoft Excel file. Dose-activity curves and $EC_{50}$ values are calculated using the program XL.Fit according to the instructions of the manufacturer (IDBS).

The results for the activity of the compounds of formula I according to the invention are listed in Table I below:

TABLE I

| Example No. | EC50 PPARα [nM] |
|---|---|
| I | 1 |
| II | 0.3 |
| IV | 0.3 |
| VII | 4 |
| X | 0.5 |
| XIX | 16 |
| XXIV | 0.9 |
| XXV | 13 |
| XXVIII | 14 |
| XXIX | 32 |
| XXXII | 0.97 |
| XXXIV | 0.82 |
| XXXVI | 0.62 |
| XXXVIII | 0.57 |
| XLI | 0.6 |
| XLIII | 0.58 |
| XLIV | 0.93 |
| XLV | 10 |
| XLVI | 0.56 |
| XLVII | 1.1 |

It is evident from Table I that the compounds of formula I according to the invention activate the PPARα receptor, thus effecting, analogously to clinically used fibrates, a lowering of the triglyceride concentration in the organism (see, for example, J.-Ch. Fruchard et al.: PPARS, Metabolic Disease and Atherosclerosis, Pharmacological Research, Vol. 44, No. 5, 2001; S. Kersten et al.: Roles of PPARs in health and disease, NATURE, VOL 405, MAY 25, 2000; I. Pineda et al.: Peroxisome proliferator-activated receptors: from transcriptional control to clinical practice, Curr Opin Lipidol 12: 2001, 245–254).

The examples given below serve to illustrate the invention, but without limiting it. Any measured melting points or decomposition points (m.p.) are uncorrected and, in general, depend on the heating rate.

EXAMPLE I

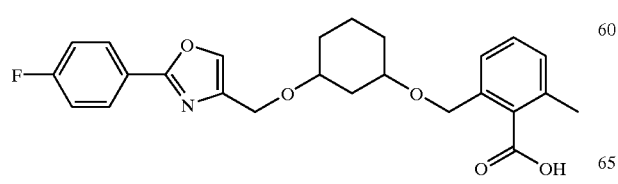

3-[2-(4-Fluorophenyl)oxazol4-ylmethoxy]cyclohexanol 3

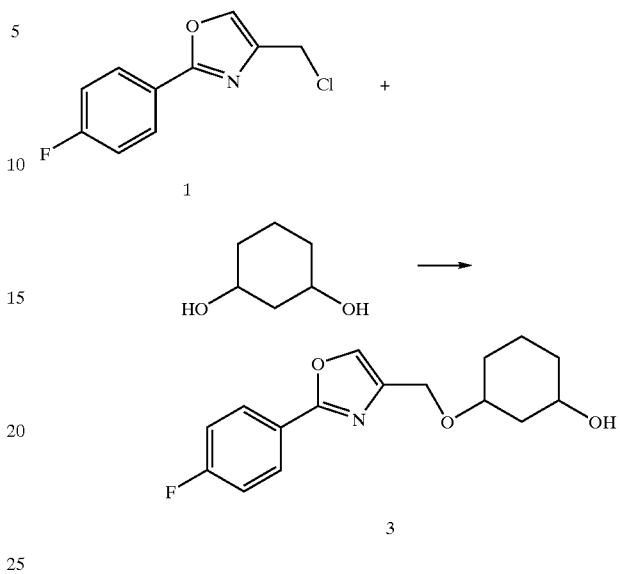

With ice-cooling, initially 2.25 g of an 80 percent suspension of sodium hydride and then 5.8 g of 1,3-cyclohexanediol were added to a mixture of 50 ml of dimethylformamide and 50 ml of tetrahydrofuran. The mixture was stirred at about 25° C. for 3 hours. 10.5 g of 4-chloromethyl-2-(4-fluorophenyl)oxazole (1) was then added, the mixture was heated at 70° C. and the reaction was monitored by thin-layer chromatography. After the reaction ended, the mixture was poured into ice-water and extracted with ethyl acetate. The organic phase was separated off, dried and concentrated and the residue was purified on silica gel by flash chromatography (ethyl acetate/n-heptane=1:1). This gave the alcohol 3 as an oil. $C_{16}H18FNO3$ (291.33) MS(ESI): 292 (M+H⁺).

Methyl 2-{3-[2-(4-fluorophenyl)oxazol-4-ylmethoxy]cyclohexyloxy}-6-methylbenzoate

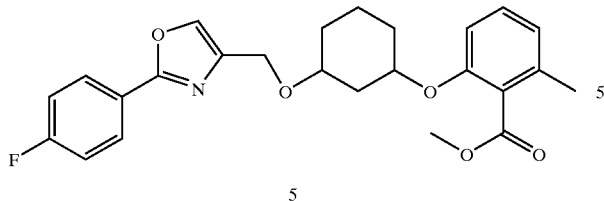

5

With ice-cooling, 0.3 g of a sodium hydride suspension (80%) were introduced into a mixture of 10 ml of dimethylformamide and 20 ml of tetrahydrofuran. 1 g of alcohol 3 in 5 ml of tetrahydrofuran was then added, and the mixture was stirred at room temperature for 1 hour. 0.8 g of bromide 4 was then added, and the mixture was stirred at room temperature and with monitoring by TLC for 3–5 hours until the conversion was substantially complete. The mixture was poured into ice-water and extracted 3 times with ethyl acetate, the organic phase was washed with 20 ml portions of water, dried over sodium sulfate and concentrated under reduced pressure at 20 mbar for approximately 1 hour, and the residue was purified by silica gel chromatography (ethyl acetate:n-heptane=1:2). This gave the methyl ester 5 as an oil. $C_{26}H_{28}FNO_5$ (453.52) MS(ESI): 454 (M+H$^+$).

2-{3-[2-(4-Fluorophenyl)oxazola4-ylmethoxy]cyclohexyloxy}-6-methylbenzoic Acid 6

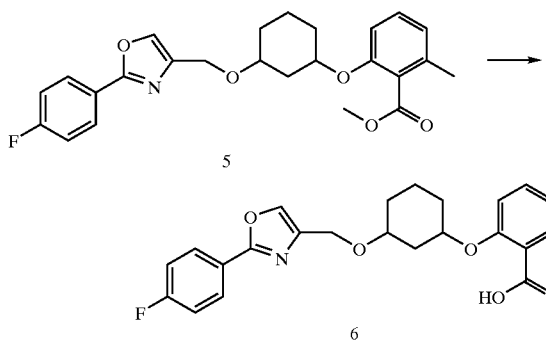

2 g of ester 5 were heated at reflux in 150 ml of tert-butanol and 24 ml of 50 percent aqueous potassium hydroxide solution for 6 hours. ⅘ of the butanol was removed under reduced pressure and the mixture was diluted with water and acidified with ice-cooling. The product was extracted with dichloromethane, dried over sodium sulfate and concentrated under reduced pressure, giving, by filtration of the residue through silica gel (CH$_2$Cl$_2$/MeOH=20:1), the acid 6 $C_{25}H_{26}FNO_5$ (432.42) MS(ESI): 433 (M+H$^+$).

EXAMPLE II

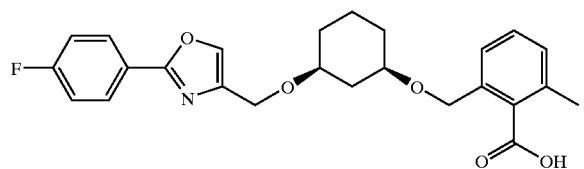

2-(4-Fluorophenyl)-4-iodomethyloxazole 2

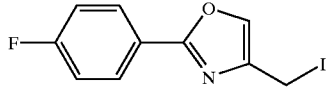

At 120° C., 31 g (123 mmol) of p-fluorobenzamide and 33 g (123 mmol) of 1,3-dichloroacetone were stirred in the absence of a solvent for 2 hours. After cooling to room temperature, the product was dissolved in 250 ml of ethyl acetate. This solution was diluted with 400 ml of n-heptane and washed 3 times with saturated NaCl solution. The organic phase was filtered through 250 ml of silica gel, and the filter pad was then washed with 200 ml of n-heptane/ethyl acetate (4:1). The solvent was distilled off, giving 4-chloromethyl-2-(4-fluorophenyl)oxazole 1 as crude product. This was dissolved in 650 ml of acetone, and 90 g of NaI were then added. The mixture was then heated at reflux for 16 hours, most of the solvent was then removed and the solid residue was suspended in 200 ml of n-heptane/ethyl acetate (1:1) and filtered through 200 ml of silica gel. The precipitate was washed with 500 ml of n-heptane/ethyl acetate (1:1), and the organic phase was concentrated. On concentration, the iodide 2 began to crystallize as white crystals. TLC n-heptane/ethyl acetate (6:1) R$_f$ 0.4 for 2 and R$_f$=0.35 for 1. $C_{10}H_7FINO$ (303.08) MS(ESI): 304 (M+H$^+$).

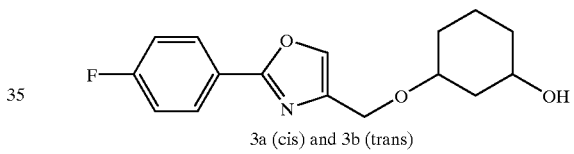

3a (cis) and 3b (trans)

10.8 g (93.1 mmol) of cis/trans-1,3-cyclohexanediol and 15.4 g (61.8 mmol) of dibutyltin oxide were heated in 800 ml of toluene on a water separator for 5 hours. 400 ml of toluene were distilled off, and the mixture was then allowed to cool to room temperature, and 280 ml of dry DMF, 15 g (49.5 mmol) of 2 and 12.7 g (80.1 mmol) of dry CsF were then added successively. The heterogeneous mixture was stirred at room temperature for 20 hours (TLC control starting material 2). 200 ml of ethyl acetate were added, and the mixture was washed three times with saturated NaCl solution. The organic phase was filtered through 150 ml of silica gel and concentrated. Following addition of n-heptane/ethyl acetate (6:1), the residue crystallized. Further recrystallization from n-heptane/ethyl acetate gave the product 3a (mixture of cis-enantiomers). The mixture of trans-enantiomers 3b was obtained from the mother liquor after concentration and chromatography. TLC n-heptane/ethyl acetate (1:1). R$_f$ 3a (cis)=0.2, R$_f$ 3b (trans)=0.3. $C_{16}H_{18}FNO_3$ (291.33) MS(ESI): 292 (M+H$^+$).

The pair of enantiomers 3a was separated by chiral HPLC. The dextrorotatory (+)-enantiomer (+)3a eluted first, followed by the levorotatory (−)-enantiomer (−)3a (Chiralpak AD 250 ×4.6; acetonitrile/methanol (9:1)).

The absolute stereochemistry was assigned by X-ray structural analysis of the camphanic acid esters of the separated diastereomers 3.

Methyl cis-2-(3-(2-(4-fluorophenyl)oxazol-4-ylmethoxy)cyclohexyloxymethyl)-6-methylbenzoate 5b

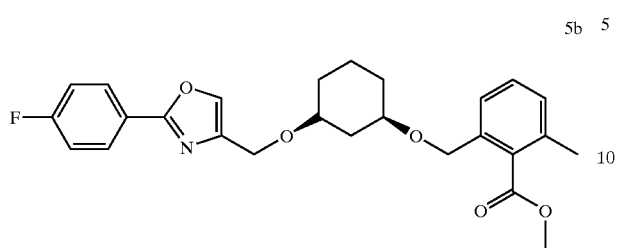

5b 1.05 g (3.6 mmol) of (−)3a, 1.3 g (5.4 mmol) 4 and 130 mg of Kl were dissolved in 12 ml of dry DMF. 140 mg (5.7 mmol) of 95% NaH were added, and the mixture was then stirred at room temperature for 1 hour. To achieve better yields with respect to the starting material (−)3a, 2 more times, the same amount of 4 and NaH were added, and the mixture was in each case stirred for 1 hour. The mixture was then allowed to stand overnight. The reaction solution was diluted with 150 ml of ethyl acetate and poured into 50 ml of water. The mixture was washed 2 more times with NaCl solution, and the organic phase was then filtered through silica gel and concentrated, and the residue was purified by flash chromatography (n-heptane/ethyl acetate, 1:1). This gave 5b as a colorless amorphous solid. TLC n-heptane-ethyl acetate (1:1). $R_f$=0.5. $C_{26}H_{28}FNO_5$ (453.52) MS(ESI): 454 (M+H$^+$).

(+)-cis-2-(3-(2-(4-Fluorophenyl)oxazol4-ylmethoxy)cyclohexyloxymethyl)-6-methylbenzoic Acid 6b

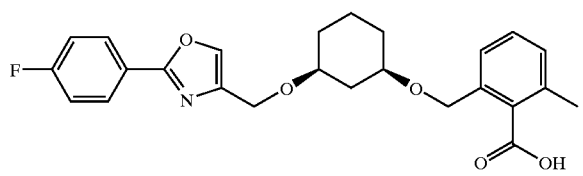

6b 4.2 g (9.2 mmol) of 5b were dissolved in 120 ml of t-BuOH. 50 ml of 50% aq. KOH were added, and the mixture was then boiled at 100° C. for 24 hours. For work-up, the mixture was allowed to cool and then diluted with 100 ml of ethyl acetate. The aqueous phase was made slightly acidic by addition of 2 N aqueous HCl and extracted 2 more times with 100 ml of ethyl acetate. The organic phase was dried over MgSO$_4$, filtered and concentrated, and the residue was purified by flash chromatography (methylene chloride/methanol/conc. ammonia, 30/5/1). This gave 6b as a white amorphous solid. TLC (methylene chloride/methanol/conc. ammonia, 30/5/1). $R_f$=0.3. Recrystallization from toluene. $C_{25}H_{26}FNO_5$ (432.42) MS(ESI): 433 (M+H$^+$).

EXAMPLE III

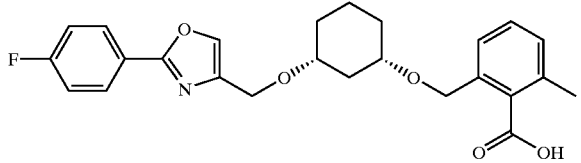

6a (−)-cis-2-{3-[2-(4-Fluorophenyl)oxazol-4-ylmethoxy]cyclohexyloxymethyl}-6-methyl-benzoic Acid 6a Using (+)3a and methyl 2-bromomethyl-6-methylbenzoate 4 as starting materials in the procedure of Example I gave the product 6a of molecular weight 432.42 ($C_{25}H_{26}FNO_5$); MS(ESI): 433 (M+H$^+$).

EXAMPLE IV

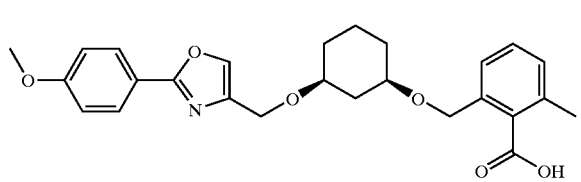

7b cis-2-(3-(2-(4-Methoxyphenyl)oxazol-4-ylmethoxy)cyclohexyloxymethyl)-6-methylbenzoic Acid 7b 170 mg (0.39 mmol)of6b were heated in 4 ml of 5.6 M NaOMe/MeOH solution at an oil bath temperature of 120° C. for 20 hours. Ethyl acetate and 2 N HCl were added, and the mixture was then worked up analogously to the synthesis of 6b. This gave 7b as a colorless amorphous solid. TLC: (methylene chloride/-methanol/conc. ammonia, 30/5/1). $R_f$~0.3. $C_{26}H_{29}NO_6$ (451.52) MS(ESI): 452 (M+H$^+$).

In the same manner, 6a gave the stereoisomeric 7a:

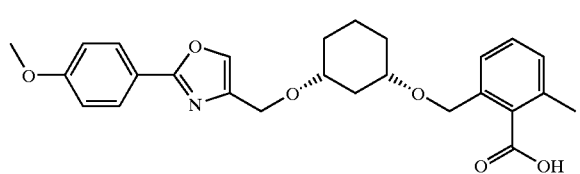

7a

TLC: (methylene chloride/methanol/conc. ammonia, 30/5/1). $R_f$~0.3. $C_{26}H_{29}NO_6$ (451.52) MS(ESI): 452 (M+H$^+$).

EXAMPLE V (11a) and EXAMPLE VI (11b)

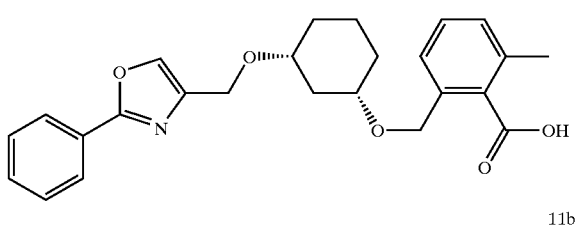

11a

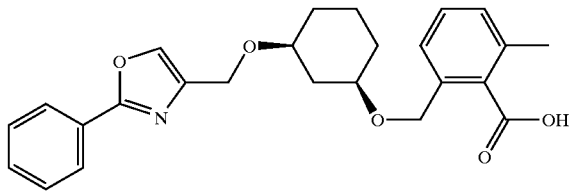

11b cis-3-(2-Phenyloxazol-4-ylmethoxy)cyclohexanol 12a,b

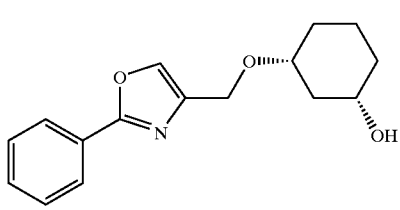

12a

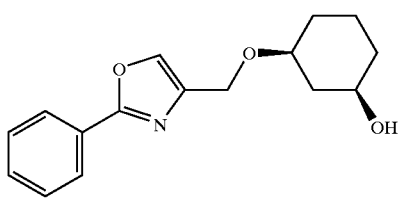

12b 1,3-Cyclbhexanediol and 4-iodomethyl-2-phenyloxazole gave the racemate 12 of molecular weight 273.33 ($C_{16}H_{19}NO_3$); MS(ESI): 274 (M+H$^+$).

The enantiomers were separated by HPLC on a chiral column. The (+)-enantiomer 12a eluted first, followed by the (−)-enantiomer 12b (Chiralpak OD 250×4.6; n-heptane:ethanol:acetonitrile=110:2:1+0.05% trifluoroacetic acid).

Methyl cis-2-methyl-6-[3-(2-phenyloxazol-4-ylmethoxy)cyclohexyloxymethyl]-benzoate 13a

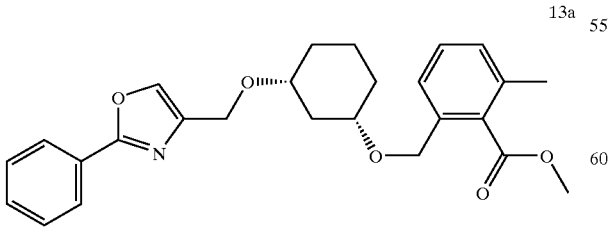

13a 12a and methyl 2-bromomethyl-6-methylbenzoate gave 13a of molecular weight 435.52 ($C_{26}H_{29}NO_5$); MS(ESI): 436 (M+H$^+$).

Methyl cis-2-methyl-6-[3-(2-phenyloxazol-4-yl methoxy)cyclohexyloxymethyl]-benzoate 13b

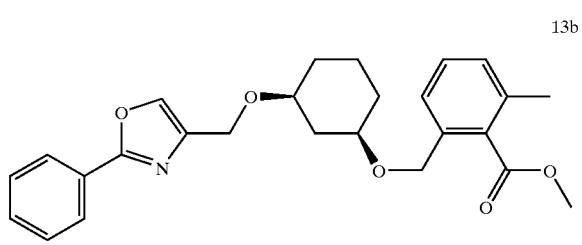

13b 12b and methyl 2-bromomethyl-6-methylbenzoate gave 13b of molecular weight 435.52 ($C_{26}H_{29}NO_5$); MS(ESI): 436 (M+H$^+$).

Cis-2-Methyl-6-[3-(2-phenyloxazol4-ylmethoxy)cyclohexyloxymethyl]benzoic Acid 11a Hydrolysis of 13a gave 11a of molecular weight 421.50 ($C_{25}H_{27}NO_5$); MS(ESI): 422 (M+H$^+$).

Cis-2-Methyl-6-[3-(2-phenyloxazola4-ylmethoxy)cyclohexyloxymethyl]benzoic Acid 11b Analogously by hydrolysis, 13b gave 11b of molecular weight 421.50 ($C_{25}H_{27}NO_5$); MS(ESI): 422 (M+H$^+$).

EXAMPLE VII (14a) and EXAMPLE VIII (14b)

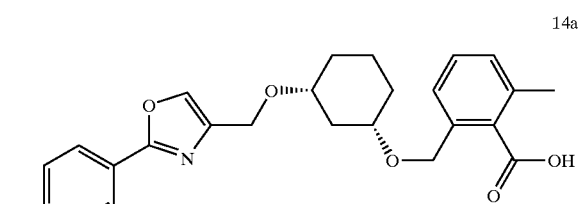

14a

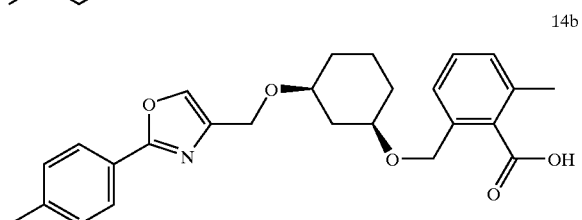

14b

Cis-3-(2-p-Tolyloxazol-4-ylmethoxy)cyclohexanol 15a,b

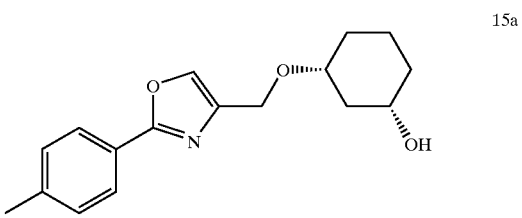

15a

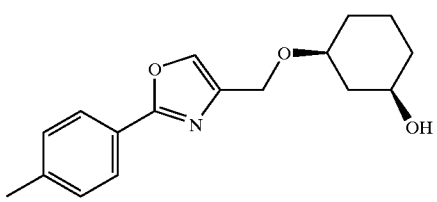
15b

Cyclohexanediol and 4-iodomethyl-2-p-tolyloxazole gave the racemate 15 of molecular weight 287.36 ($C_{17}H_{21}NO_3$); MS(ESI): 288 (M+H$^+$).

Separation of the enantiomers was carried out by HPLC on a chiral column. The (+)-enantiomer 15a eluted first, followed by the (−)-enantiomer 15b (Chiralpak OD250×4.6; n-heptane:ethanol:acetonitrile=110:5:1+0.05% trifluoroacetic acid).

Methyl cis-2-methyl-6-[3-(2-p-tolyloxazol4-ylmethoxy)cyclohexyloxymethyl]-benzoate 16a

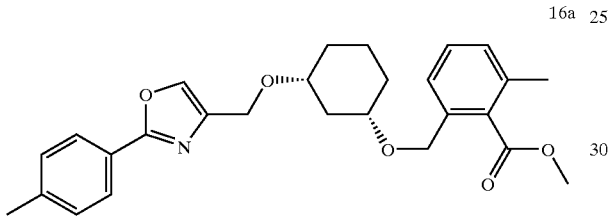
16a 15a and methyl 2-bromomethyl-6-methylbenzoate gave 16a of molecular weight 449.55 ($C_{27}H_{31}NO_5$); MS(ESI): 450 (M+H$^+$).

Methyl cis-2-methyl-6-[3-(2-p-tolyloxazol4-ylmethoxy)cyclohexyloxymethyl]benzoate 16b

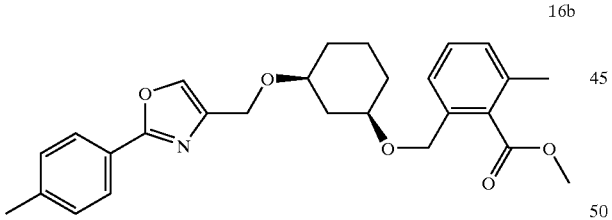
16b 15b and methyl 2-bromomethyl-6-methylbenzoate gave 16b of molecular weight 449.55 ($C_{27}H_{31}NO_5$); MS(ESI): 450 (M+H$^+$).

Cis-2-Methyl-6-[3-(2-p-tolyloxazol4-ylmethoxy)cyclohexyloxymethyl]benzoic Acid 14a 16a gave 14a of molecular weight 435.52 ($C_{26}H_{29}NO_5$); MS(ESI): 436 (M+H$^+$).

Cis-2-Methyl-6-[3-(2-p-tolyloxazla4-ylmethoxy)cyclohexyloxymethyi]benzoic Acid 14b 16b gave the product 14b of molecular weight 435.52, ($C_{26}H_{29}NO_5$); MS(ESI): 436 (M+H$^+$).

EXAMPLE IX (17a) and EXAMPLE X (17b)

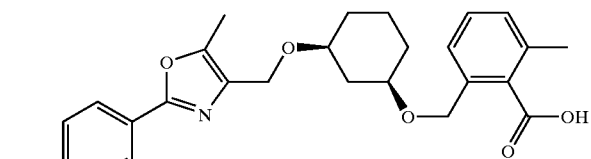
17a

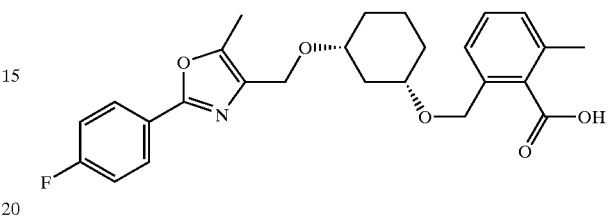
17b

Cis-3-[2-(4-Fluorophenyl)-5-methyloxazol4-ylmethoxy]cyclohexanol 18a,b

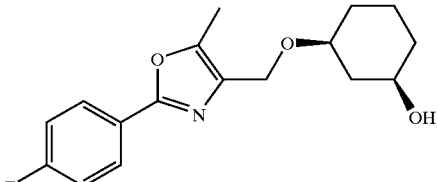
18a

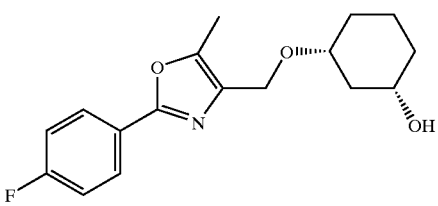
18b

Cyclohexanediol and 2-(4-fluorophenyl)-4-iodomethyl-5-methyloxazole gave the racemate 18 of molecular weight 305.35 ($C_{17}H_{20}FNO_3$); MS(ESI): 306 (M+H$^+$).

The enantiomers were separated by HPLC on a chiral column. The (+)-enantiomer 18a eluted first, followed by the (−)-enantiomer 18b (Chiralpak OD 250×4.6; n-heptane:ethanol:acetonitrile=110:2:1+0.05% trifluoroacetic acid).

Methyl cis-2-{3-[2-(4-fluorophenyl)-5-methyloxazol-4-ylmethoxy]cyclohexyloxymethyl}-6-methylbenzoate 19a

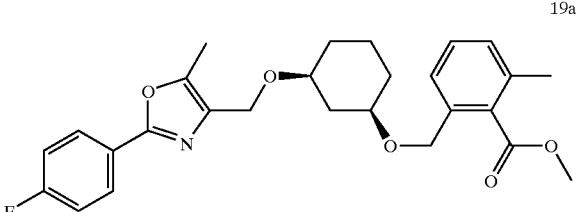
19a 18a and methyl 2-bromomethyl-6-methylbenzoate gave 19a of molecular weight 467.54 ($C_{27}H_{30}FNO_5$); MS(ESI): 468 (M+H$^+$).

Methyl cis-2-{3-[2-(4-fluorophenyl)-5-methyloxazol-4-ylmethoxy]-cyclohexyloxymethyl}-6-methylbenzoate 19b

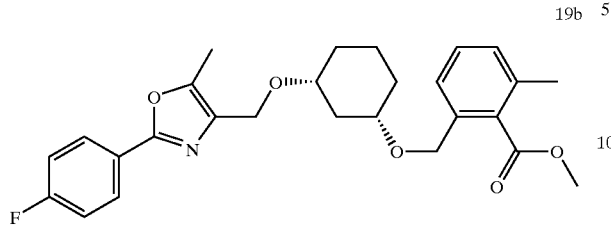

18b and methyl 2-bromomethyl-6-methylbenzoate gave 19b of molecular weight 467.54 (C$_{27}$H$_{30}$FNO$_5$); MS(ESI): 468 (M+H$^+$).

Cis-2-(3-[2-(4-Fluorophenyl)-5-methyloxazol4-ylmethoxy]cyclohexyloxymethyl}-6-methylbenzoic Acid 17a Hydrolysis of 19a gave 17a of molecular weight 453.52 (C$_{26}$H$_{28}$FNO5); MS(ESI): 454 (M+H$^+$).

Cis-2-{3-[2-(4-Fluorophenyl)-5-methyloxazol4-ylmethoxy]cyclohexyloxymethyl}-6-methylbenzoic Acid 17b Analogously by hydrolysis, 19b gave 17b of molecular weight 453.52 (C$_{26}$H$_{28}$FNO$_5$); MS(ESI): 454 (M+H$^+$).

EXAMPLE XI (20) and EXAMPLE XII (21)

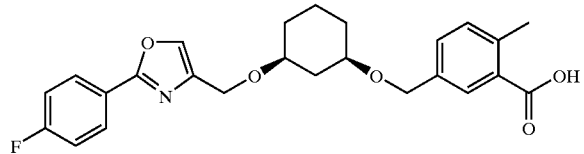

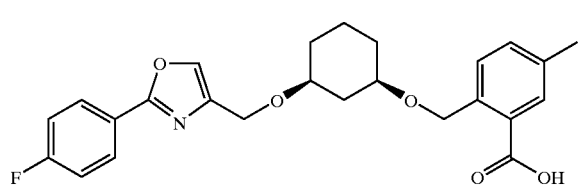

Ethyl 5-bromomethyl-2-methylbenzoate 22 and ethyl 2-bromomethyl-5-methylbenzoate 23

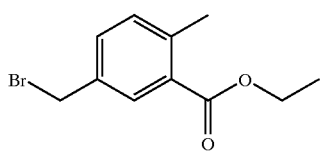

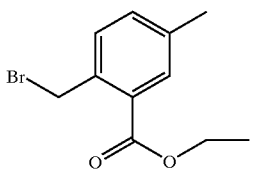

A solution of 3.5 g of ethyl 2,5-dimethylbenzoate, 3.15 g of N-bromosuccinimide and 100 ml of carbon tetrachloride was, for 3 hours, heated under reflux and irradiated with a 300 watt photolamp. The resulting precipitate was filtered off and the concentrated filtrate was chromatographed on silica gel. This gave an approximately 2:3 (22:23) mixture of the regioisomeric benzyl bromides 22 and 23 of molecular-weight 257.13 (C$_{11}$H$_{13}$BrO$_2$); MS (ESI): 257 (M+H$^+$). Ethyl rac-cis-5-{3-[2-(4-fluorophenyl)oxazol4-ylmethoxy]cyclohexyloxymethyl}-2-methylbenzoate 24 and ethyl rac-cis-2-{3-[2-(4-fluorophenyl)oxazol-4-ylmethoxy]cyclohexyloxymethyl}-5-methylbenzoate 25.

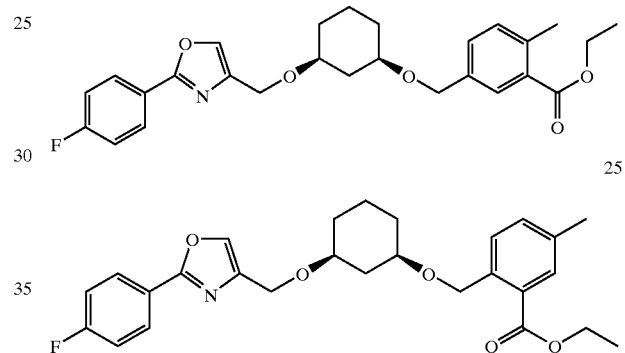

At 0° C., a solution of 150 mg of rac-cis-3-[2-(4-fluorophenyl)oxazol-4-ylmethoxy]-cyclohexanol 3a in 0.5 ml of dimethylformamide was added dropwise to a suspension of 40 mg of sodium hydride (55–65% in paraffin oil) in 1 ml of dimethylfdrmamide. After the evolution of gas ceased, 198 mg of 2:3 mixture of ethyl 5-bromomethyl-2-methylbenzoate 22 and methyl 2-bromomethyl-5-methylbenzoate 23 were added. After 30 minutes at 0° C., the mixture was allowed to react for a further 1 hour at room temperature. The mixture was poured into an ammonium chloride solution and extracted twice with MTBE. The extracts were dried over magnesium sulfate, filtered and concentrated using a rotary evaporator, and the product was then purified by silica gel chromatography (mobile phase: n-heptane/ethyl acetate 3:1). This gives the faster eluting product ethyl rac-cis-2-{3-[2-(4-fluorophenyl)oxazol-4-ylmethoxy]cyclohexyloxymethyl}-5-methylbenzoate 25 of molecular weight 467.54 (C$_{27}$H$_{30}$FNO$_5$); MS (ESI): 468 (M+H$^+$).

Also isolated was the later eluting product ethyl rac-cis-5-{3-[2-(4-fluorophenyl)oxazol-4-ylmethoxy]cyclohexyloxymethyl}-2-methylbenzoate 24 of molecular weight 467.54 (C$_{27}$H$_{30}$FNO$_5$); MS (ESI): 468 (M+H$^+$).

Rac-cis-5-{3-[2-(4-Fluorophenyl)oxazol-4-ylmethoxy]cyclohexyloxymethyl}-2-methylbenzoic Acid 20

A suspension of 47 mg of ethyl rac-cis-5-{3-[2-(4-fluorophenyl)oxazol-4-ylmethoxy]cyclohexyloxymethyl}-

2-methylbenzoate 24, 2 ml of 1,1-dimethylethanol and 50% (w/w) potassium hydroxide was heated at 85° C. (oil bath) for 2 hours. The pH was adjusted to 3 using dilute hydrochloric acid and the mixture was extracted twice with MTBE. The extracts were dried over magnesium sulfate, filtered and concentrated on a rotary evaporator, and the product was then purified by chromatography. This gave the product 20 of molecular weight 439.49 ($C_{25}H_{26}FNO5$); MS (ESI): 440 (M+H$^+$).

Using a different starting material in the procedure for making 20:

rac-cis-2-{3-[2-(4-Fluorophenyl)oxazol-4-ylmethoxy] cyclohexyloxymethyl}-5-methylbenzoic acid 21 was prepared from ethyl rac-cis-2-{3-[2-(4-fluorophenyl) oxazol4-ylmethoxy]cyclohexyloxymethyl}-5-methylbenzoate 25.

EXAMPLE XIII

Rac-trans-2-{3-[2-(4-Fluorophenyl)oxazol-4-ylmethoxy]cyclohexyloxymethyl}-6-methylbenzoic acid 26

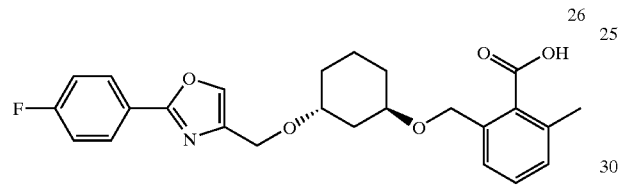

26 rac-trans 3b and methyl 2-bromomethyl-6-methylbenzoate gave the product 26 of molecular weight 439.49 ($C_{25}H_{26}FNO_5$); MS(ESI): 440 (M+H$^+$).

EXAMPLE XIV

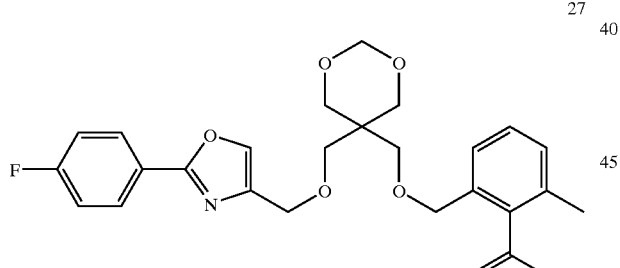

27

5-(2-(4-Fluorophenyl)oxazol-4-ylmethoxyrmethyl)-1,3-dioxan-5-ylmethanol 28

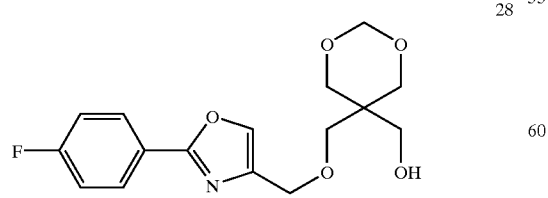

28

1.0 g (6.7 mmol) of 5-hydroxymethyl-1,3-dioxan-5-ylmethanol and 0.5 g (16.5 mrpol) of 2 were dissolved in 20 ml of dry DMF. 300 mg of 55% NaH in paraffin oil were added, and the mixture was then stirred at room temperature for 1 hour. Work-up-was carried out analogously to the synthesis of compound 5b. This gave 28 as a white amorphous solid. TLC (n-heptane/ethyl acetate 1:2). R$_f$=0.4. $C_{16}H_{18}FNO_5$ (323.33) MS(ESI) 324.2 (M+H$^+$).

Methyl 2-{5-[2-(4-fluorophenyl)oxazol4-ylmethoxymethyl]-1,3-dioxan-5-ylmethoxymethyl}-6-methylbenzoate 29

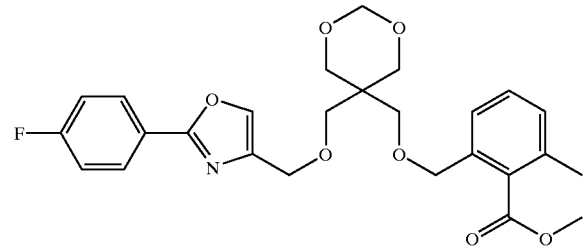

29

Using 28 and 4 as starting materials in the synthesis procedure of 5b of Example II gave compound 29.

2-{5-[2-(4-Fluorophenyl)oxazol4-ylmethoxymethyl]-1,3-dioxan-5-ylmethoxymethyl}-6-methylbenzoic Acid 27

Using 29 as a starting material in the synthesis procedure for 6b of Example II gave compound 27 by hydrolysis.

EXAMPLE XV

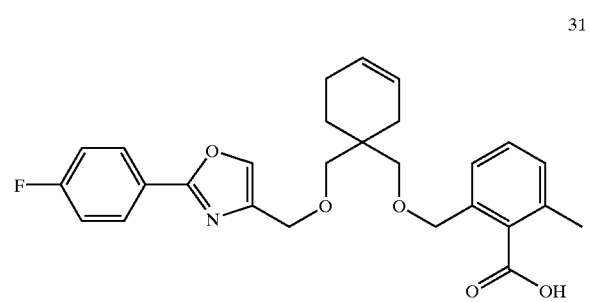

31

2-{1-[2-(4-Fluorophenyl)oxazol4-ylmethoxymethyl] cyclohex-3-enylmethoxymethyl}-6-methylbenzoic Acid 31 using (1-hydroxymethylcyclohex-3-enyl)methanol,iodide 2 and bromide 4 as starting in the procedure of Example XIV, gave the product 31 of molecular weight 465.53 ($C_{27}H_{28}FNO_5$); MS(ESI): 466 (M+H$^+$).

EXAMPLE XVI

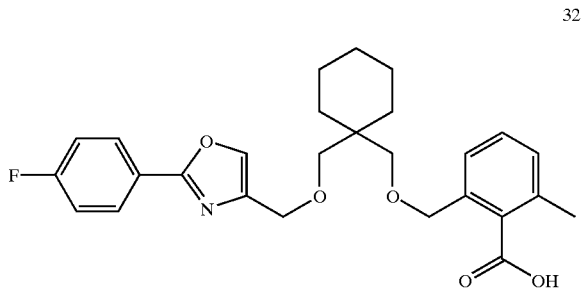

2-{1-[2-(4-Fluorophenyl)oxazol-4-ylmethoxymethyl]cyclohexylmethoxymethyl}-6-methylbenzoic Acid 32

Using (1-hydroxymethylcyclohexyl)methanol, iodide 2, and bromide 4 as reactants in the procedure of Example XIV gave the product 32 of molecular weight 467.53 ($C_{27}H_{30}FNO_5$); MS(ESI): 468 (M+H$^+$).

EXAMPLE XVII

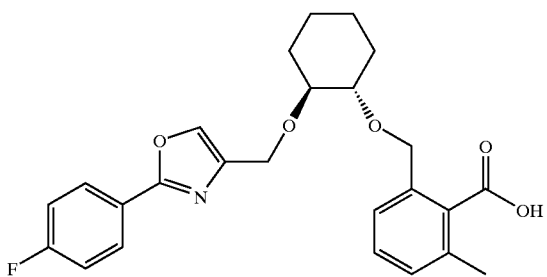

Rac-trans-2-{2-[2-(4-Fluorophenyl)oxazol-4-ylmethoxy]cyclohexyloxymethyl}-6-methylbenzoic Acid 33

Using trans-1,2-dihydroxycyclohexanol, iodide 2 and bromide 4 as starting materials in the synthesis procedure of Example XIV, gave the desired product 33 of molecular weight 439.49 ($C_{25}H_{26}FNO_5$); MS(ESI): 440 (M+H$^+$).

EXAMPLE XVIII

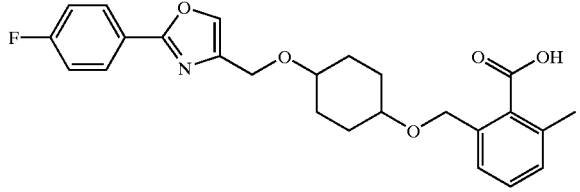

2-{4-[2-(4-Fluorophenyl)oxazol-4-ylmethoxy]cyclohexyloxymethyl}-6-methylbenzoic Acid 34

1,4-Cyclohexanediol, iodide 2 and bromide 4 gave product 34 of molecular weight 439.49 ($C_{25}H_{26}FNO_5$); MS(ESI): 440 (M+H$^+$).

EXAMPLE XIX

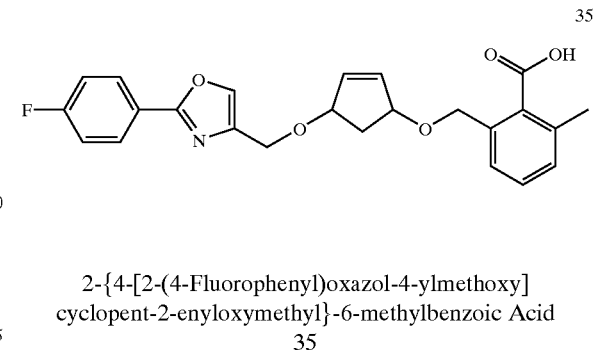

2-{4-[2-(4-Fluorophenyl)oxazol-4-ylmethoxy]cyclopent-2-enyloxymethyl}-6-methylbenzoic Acid 35

Cyclopent-2-ene-1,4-diol, iodide 2 and bromide 4 gave the product 35 of molecular weight 423.45 ($C_{24}H_{22}FNO_5$); MS(ESI): 424 (M+H$^+$).

EXAMPLE XX

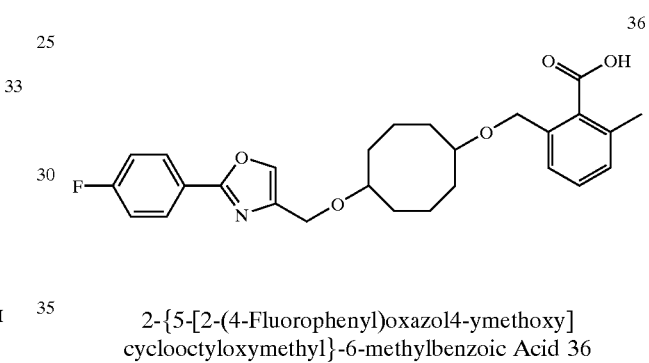

2-{5-[2-(4-Fluorophenyl)oxazol4-ymethoxy]cyclooctyloxymethyl}-6-methylbenzoic Acid 36

1,5-Cyclooctanediol, iodide 2 and bromide 4 gave product 36 of molecular weight 467.54 ($C_{27}H_{30}FNO_5$); MS(ESI): 468 (M+H$^+$).

EXAMPLE XXI

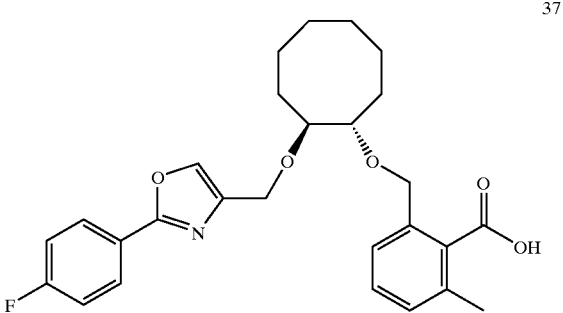

Rac-trans-2-{2-[2-(4-Fluorophenyl)oxazol-4-ylmethoxy]cyclooctyloxymethyl}-6-methylbenzoic Acid 37 trans-1,2-Cyclooctanediol, iodide 2 and bromide 4 gave the desired product 37 of molecular weight 467.54 ($C_{27}H_{30}FNO_5$); MS(ESI): 468 (M+H$^+$).

EXAMPLE XXII

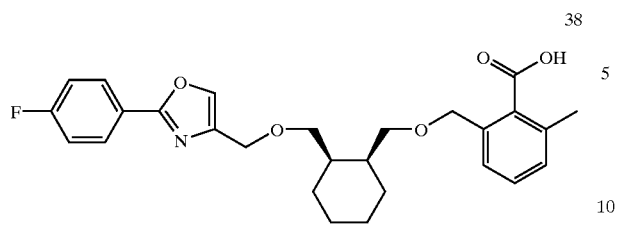

38

Rac-cis-2-{2-[2-(4-Fluorophenyl)oxazol4-ylmethoxy]methylcyclohexyl-methoxymethyl}-6-methylbenzoic Acid 38 cis-(2-Hydroxymethylcyclohexyl)methanol, iodide 2 and bromide 4 gave the product 38 of molecular weight 467.54 ($C_{27}H_{30}FNO_5$); MS(ESI): 468 (M+H$^+$).

EXAMPLE XXIII

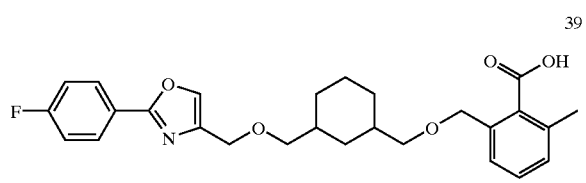

39

2-{2-[2-(4-Fluorophenyl)oxazol-4-ylmethoxy]methylcyclohexylmethoxymethyl}-6-methylbenzoic Acid 39

(3-Hydroxymethylcyclohexyl)methanol, iodide 2 and bromide 4 gave the product 39 of molecular weight 467.54 ($C_{27}H_{30}FNO_5$); MS(ESI): 468 (M+H$^+$).

EXAMPLE XXIV

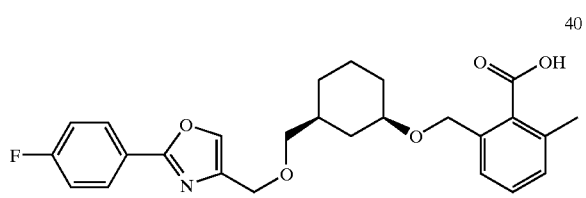

40

Rac-cis-2-{3-[2-(4-Fluorophenyl)oxazol-4-ylmethoxymethyl]cyclohexyloxymethyl}-6-methylbenzoic Acid 40 cis-3-Hydroxymethylcyclohexanol, iodide 2 and bromide 4 gave product 40 of molecular weight 453.52 ($C_{26}H_{28}FNO_5$); MS(ESI):+454 (M+H$^+$).

EXAMPLE XXV

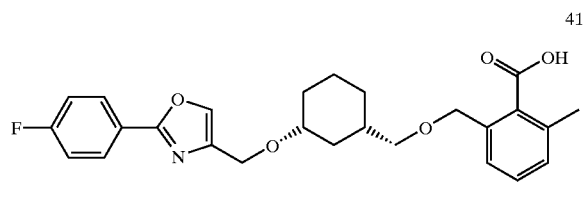

41

Rac-cis-2-{3-[2-(4-Fluorophenyl)oxazol4-ylmethoxy]cyclohexylmethoxymethyl}-6-methylbenzoic Acid 41

Reacting cis-3-hydroxymethylcyclohexanol, bromide 4 and iodide 2 in a reverse order relative to Example XXIV gave the product 41 of molecular weight 453.52 ($C_{26}H_{28}FNO_5$); MS(ESI): 454 (M+H$^+$).

EXAMPLE XXVI

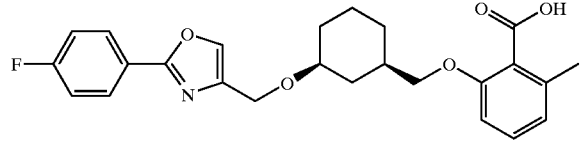

42

Rac-cis-2-{3-[2-(4-Fluorophenyl)oxazol-4-ylmethoxy]cyclohexylmethoxy}-6-methylbenzoic Acid 42 cis-3-Hydroxymethylcyclohexanol, iodide 2 and ethyl 2-hydroxy-6-methylbenzoate gave the product 42 of molecular weight 439.49 ($C_{25}H_{26}FNO_5$); MS(ESI): 440 (M+H$^+$).

EXAMPLE XXVII

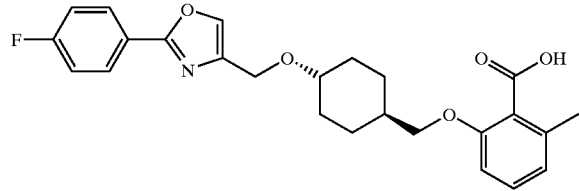

43

Rac-trans-2-{4-[2-(4-Fluorophenyl)oxazol-4-ylmethoxy]cyclohexylmethoxy}-6-methylbenzoic Acid 43 trans-4-Hydroxymethylcyclohexanol, iodide 2 and ethyl 2-hydroxy-6-methylbenzoate gave the product 43 of molecular weight 439.49 ($C_{25}H_{26}FNO_5$); MS(ESI): 440 (M+H$^+$).

EXAMPLE XXVIII

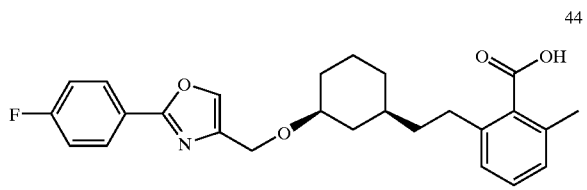

Rac-cis-2-(2-{3-[2-(4-Fluorophenyl)oxazol-4-ylmethoxy]cyclohexyl}ethyl)-6-methylbenzoic Acid
44 cis-3-Ethynylcyclohex-2-enol, ethyl 2-methyl-6-trifluoromethanesulfonyloxybenzoate and iodide 2 gave the product 44 of molecular weight 437.52 ($C_{26}H_{28}FNO_4$); MS(ESI): 438 ($M+H^+$).

EXAMPLE XXIX

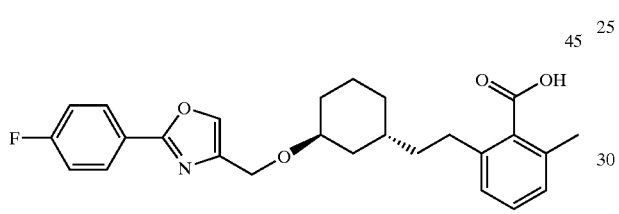

Rac-trans-2-(2-{3-[2-(4-Fluorophenyl)oxazol4-ylmethoxy]cyclohexyl}ethyl)-6-methylbenzoic Acid
45 trans-3-Ethynylcyclohex-2-enol, ethyl 2-methyl-6-trifluoromethanesulfonyloxybenzoate and iodide 2 gave the product 45 of molecular weight 437.52 ($C_{26}H_{28}FNO_4$);.MS (ESI): 438 ($M+H^+$).

EXAMPLE XXX

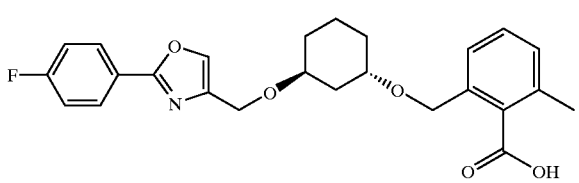

Rac-trans-2-(3-(2-(4-Fluorophenyl)oxazol4-ylmethoxy)cyclohexyloxymethyl)-6-methylbenzoic Acid 46

The racemic trans-enantiomer mixture 3b (see Example I) and methyl 2-bromomethyl-6-methylbenzoate 4 gave the desired product 46 of molecular weight 439.49 ($C_{25}H_{26}FNO_5$); MS(ESI): 440 ($M+H^+$).

EXAMPLE XXXI

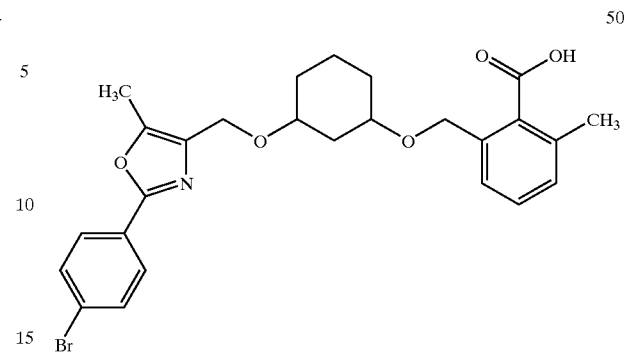

Methyl 2-(cis-3-hydroxycyclohexyloxymethyl)-6-methylbenzoate 47 and methyl 2-(trans-3-hydroxycyclohexyloxymethyl)-6-methylbenzoate 48

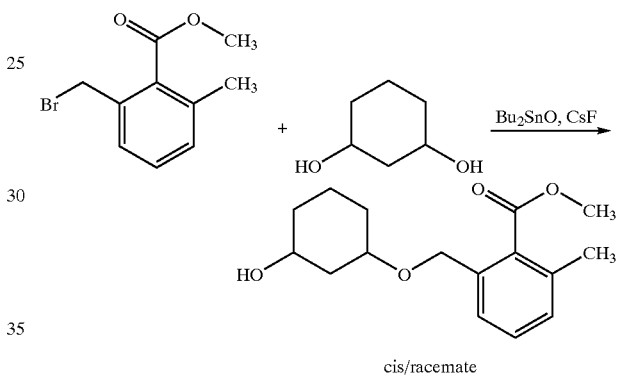

cis/racemate 8.7 g 1,3-cyclohexanediol and 12 g dibutyltin oxide were dissolved in 600 ml of toluene and, under reflux on a water separator, heated to boiling. During the reaction, the reaction volume was reduced to half of the original volume. After 4 hours, the reaction mixture was cooled to room temperature, and 300 ml of DMF, 9.0 g of methyl 2-bromomethyl-6-methylbenzoate and 9.4 g of cesium fluoride were added. The mixture was stirred at room temperature for 12 hours. The reaction mixture was diluted by addition of ethyl acetate and washed with saturated NaCl solution. The organic phase was dried over magnesium sulfate, the solvent was removed under reduced pressure and the residue was purified by flash chromatography on silica gel (n-heptane/ethyl acetate= 50:1→1:2). This gave about 6 g of the alcohol 47 (cis-racemate) as an oil. $C_{16}H_{22}O_4$ (278.35), MS(ESI): 279 ($M+H^+$). The unreacted trans-1,3-cyclohexanediol also eluted from the chromatography column. It was alkylated analogously to Example I using sodium hydride and methyl 2-bromomethyl-6-methylbenzoate. After analogous work-up and chromatography as described for the cis-racemate, the trans-racemate 48 was obtained $C_{16}H_{22}O_4$ (278.35), MS(ESI): 279 ($M+H^+$).

Racemates 47 and 48 were separated by chromatography on a chiral phase (Chiralpak AD/2 250×4.6; n-heptane:ethanol:methanol=25:1:0.5+0.1 % trifluoroacetic acid, $R_t$ (47a)=8.9 min; retention time of the enantiomer: $R_t$ (47b)=9.9 min (the absolute retention times varied with the exact chromatography conditions)).

The reactions described below can be carried out both with the pure stereoisomers and with mixtures of the stereoisomers.

Methyl 2-{3-[2-(4-bromophenyl)-5-methyloxazol-4-ylmethoxy]cyclohexyloxymethyl}-6-methylbenzoate 49

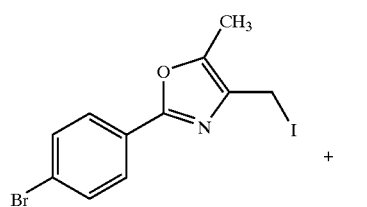

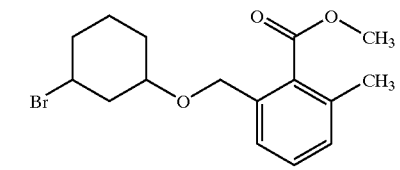

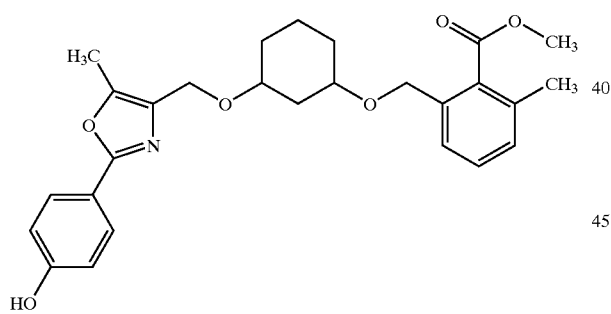

At room temperature, 50 mg of a 60% sodium hydride suspension and then 408 mg of 2-(4-bromophenyl)4-iodomethyl-5-methyloxazole were added to a solution of 200 mg of methyl 2-(3-hydroxycyclohexyloxymethyl)-6-methylbenzoate in 5 ml of dimethylformamide. After one hour, methyl tert-butyl ether was added, and the mixture was extracted with water. The organic phase was dried over magnesium sulfate, the solvents were removed under reduced pressure and the residue was purified by RP-HPLC. This gave 49 as a light-yellow oil. $C_{27}H_{30}BrNO_5$ (528.45), MS(ESI): 528.2, 530.2 (M+H$^+$).

2-{3-[2-(4-Bromophenyl)-5-methyloxazol-4-ylmethoxy]cyclohexyloxymethyl}-6-methylbenzoic Acid 50

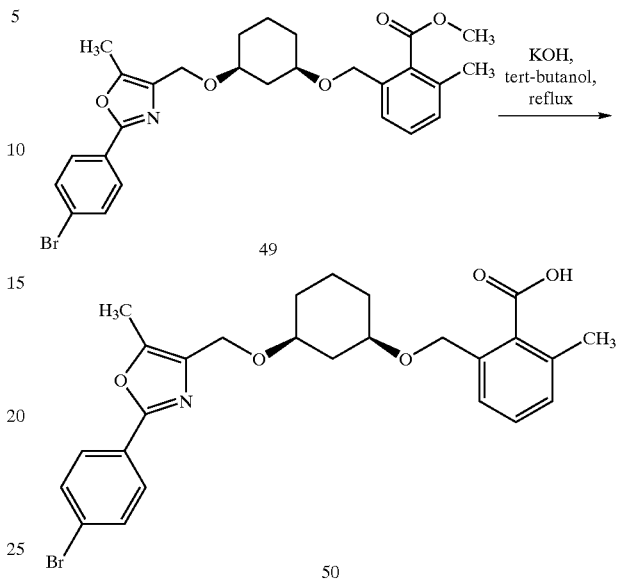

117 mg of 49 were stirred in a mixture of 10 ml of tert-butanol and 1 ml of 10 N aqueous potassium hydroxide solution at 90° C. After two days, the mixture was acidified with hydrochloric acid and extracted with ethyl acetate. The combined organic phases were dried over magnesium sulfate, the solvents were removed under reduced pressure and the residue was purified by RP-HPLC. This gave 50 as an amorphous solid. $C_{26}H_{28}BrNO_5$ (514.52), MS(ESI): 514.29, 516.29 (M+H$^+$).

EXAMPLE XXXII

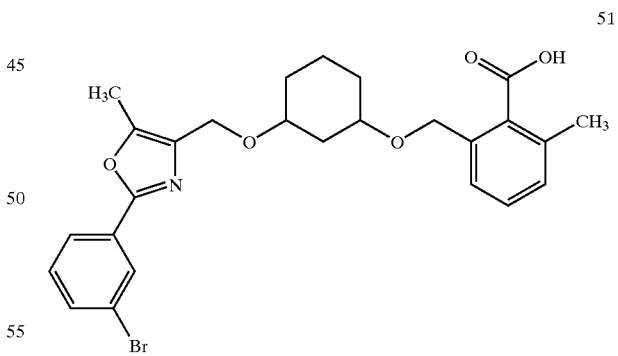

2-{3-[2-(3-Bromophenyl)-5-methyloxazol-4-ylmethoxy]cyclohexyloxymethyl}-6-methylbenzoic Acid 51

Using methyl 2-(3-hydroxycyclohexyloxymethyl)-6-methylbenzoate and 2-(3-bromophenyl)-4-iodomethyl-5-methyloxazole as starting materials in the procedure of Example XXXI, gave the product 51 of molecular weight 514.42, ($C_{26}H_{28}BrNO_5$), MS(ESI): 514.30, 516.30 (M+H$^+$).

EXAMPLE XXXIII

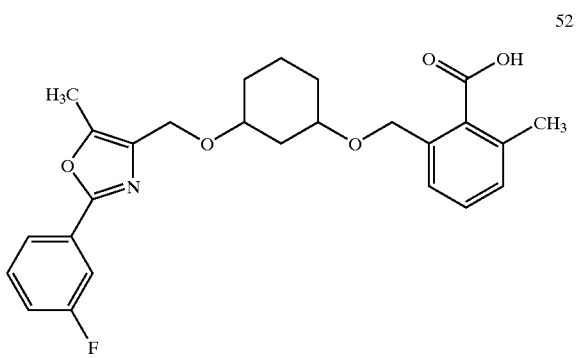

2-{3-[2-(3-Fluorophenyl)-5-methyloxazol-4-ylmethoxy]cyclohexyloxymethyl}-6-methylbenzoic Acid 52

Using methyl 2-(3-hydroxycyclohexyloxymethyl)-6-methylbenzoate and 2-(3-fluorophenyl)-4-iodomethyl-5-methyloxazole as starting materials in the procedure of Example XXXI, gave the product 52 of molecular weight 453.52 ($C_{26}H_{28}FNO_5$), MS(ESI): 454.35 (M+H$^+$).

EXAMPLE XXXIV

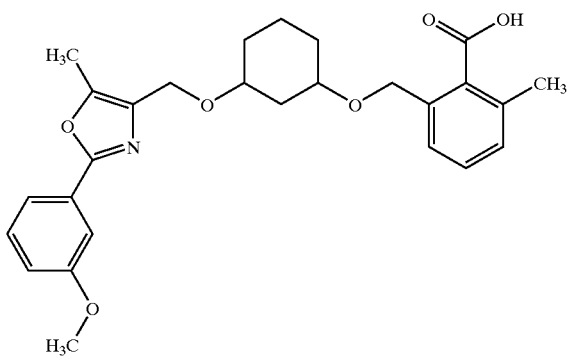

2-{3-[2-(3-Methoxyphenyl)-5-methyloxazol4-ylmethoxy]cyclohexyloxymethyl}-6-methylbenzoic Acid 53

Using methyl 2-(3-hydroxycyclohexyloxymethyl)-6-methylbenzoate and 2-(3-methoxyphenyl)4-iodomethyl-5-methyloxazole as starting materials in the procedure of Example XXXI, gave the product 53 of molecular weight 465.55 ($C_{27}H_{31}NO_6$), MS(ESI): 466.37 (M+H$^+$).

EXAMPLE XXXV

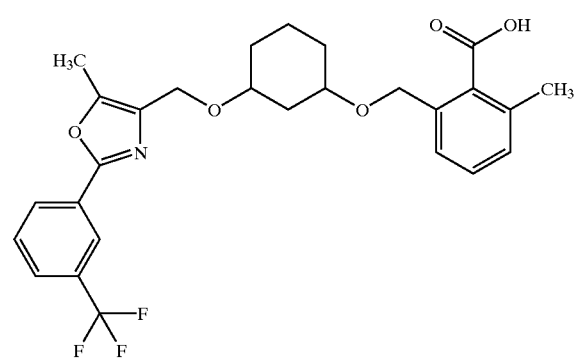

2-{3-[2-(3-Trifluoromethylphenyl)-5-methyloxazol4-ylmethoxy]cyclohexyloxymethyl}-6-methylbenzoic Acid 54

Using methyl 2-(3-hydroxycyclohexyloxymethyl)-6-methylbenzoate and 2-(3-trifluoromethylphenyl)4-iodomethyl-5-methyloxazole as starting materials in the procedure of Example XXXI, gave the product 54 of molecular weight 503.52 ($C_{27}H_{28}F_3NO_5$), MS(ESI): 504.37 (M+H$^+$).

EXAMPLE XXXVI

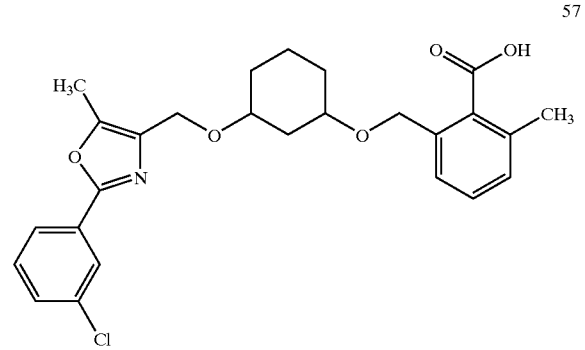

2-{3-[2-(3-Chlorophenyl)-5-methyloxazol4-ylmethoxy]cyclohexyloxymethyl}-6-methylbenzoic Acid 57

Using methyl 2-(3-hydroxycyclohexyloxymethyl)-6-methylbenzoate and 2-(3-chlorophenyl)4-iodomethyl-5-methyloxazole as starting materials in the procedure of Example XXXI, gave the product 57 of molecular weight 469.97 ($C_{26}H_{28}ClNO_5$), MS(ESI): 470.43 (M+H$^+$).

EXAMPLE XXXVII

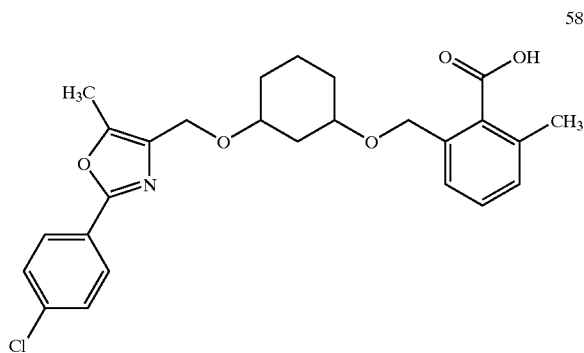

58

2-{3-[2-(4-Chlorophenyl)-5-methyloxazol-4-yl methoxy]cyclohexyloxymethyl}-6-methylbenzoic Acid 58

Using methyl 2-(3-hydroxycyclohexyloxymethyl)-6-methylbenzoate and 2-(4-chlorophenyl)4-iodomethyl-5-methyloxazole as starting materials in the procedure of Example XXXI, the product 58 of molecular weight 469.97 ($C_{26}H_{28}ClNO_5$), MS(ESI): 470.40 (M+H$^+$).

EXAMPLE XXXVIII

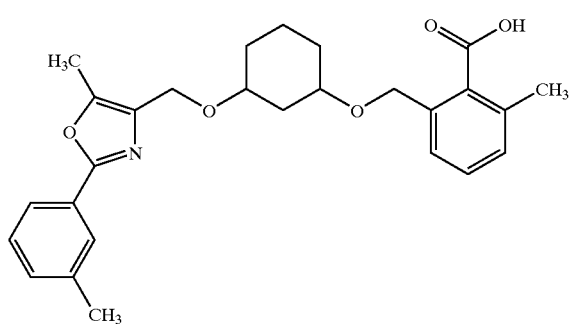

59

2-{3-[2-(3-Methylphenyl)-5-methyloxazol-4-ylmethoxy]cyclohexyloxymethyl}-6-methylbenzoic Acid 59

Using methyl 2-(3-hydroxycyclohexyloxymethyl)-6-methylbenzoate and 2-(3-methylphenyl)-4-iodomethyl-5-methyloxazole as starting materials in the procedure of Example XXXI, gave the product 59 of molecular weight 449.55 ($C_{27}H_{31}NO_5$), MS(ESI): 450.53 (M+H$^+$).

EXAMPLE XXXIX

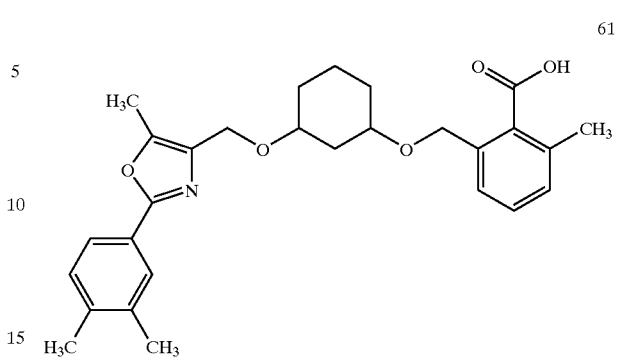

61

2-{3-[2-(3,4-Dimethylphenyl)-5-methyloxazol4-ylmethoxy]cyclohexyloxymethyl}-6-methylbenzoic Acid 61

Using methyl 2-(3-hydroxycyclohexyloxymethyl)-6-methylbenzoate and 2-(3,4-dimethylphenyl)-4-iodomethyl-5-methyloxazole as starting materials in the procedure of Example XXXI, gave the product 61 of molecular weight 463.58 ($C_{28}H_{33}NO_5$), MS(ESI): 464.22 (M+H$^+$).

EXAMPLE XL

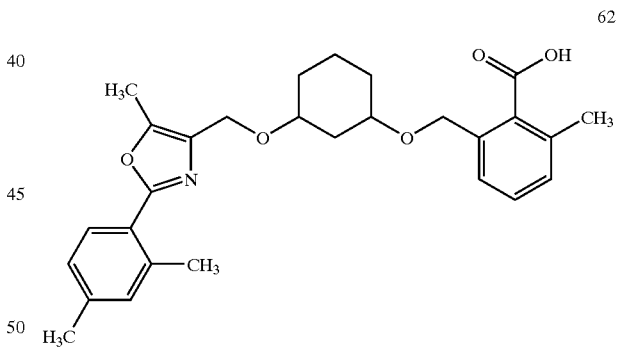

62

2-{3-(2-(2,4-Dimethylphenyl)-5-methyloxazol-4-ylmethoxy]cyclohexyloxymethyl}-6-methylbenzoic Acid 62

Using methyl 2-(3-hydroxycyclohexyloxymethyl)-6-methylbenzoate and 2-(2,4-dimethylphenyl)-4-iodomethyl-5-methyloxazole as starting materials in the procedure of Example XXXI, gave the product 62 of molecular weight 463.58 ($C_{28}H_{33}NO_5$), MS(ESI): 464.22 (M+H$^+$).

EXAMPLE XLI

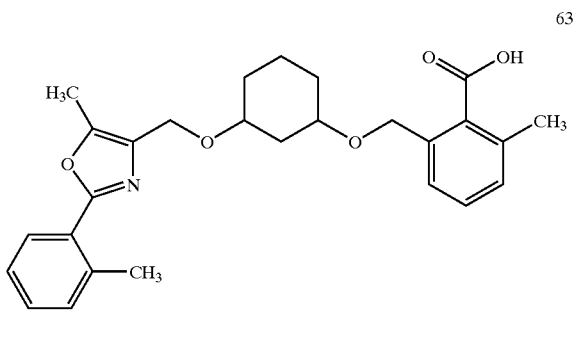

63

2-{3-[2-(2-Methylphenyl)-5-methyloxazol-4-ylmethoxy]cyclohexyloxymethyl}-6-methylbenzoic Acid 63

Using methyl 2-(3-hydroxycyclohexyloxymethyl)-6-methylbenzoate and 2-(2-methylphenyl)-4-iodomethyl-5-methyloxazole as starting materials in the procedure of Example XXXI, gave the product 63 of molecular weight 449.55 ($C_{27}H_{31}NO_5$), MS(ESI): 450.20 (M+H$^+$).

EXAMPLE XLII

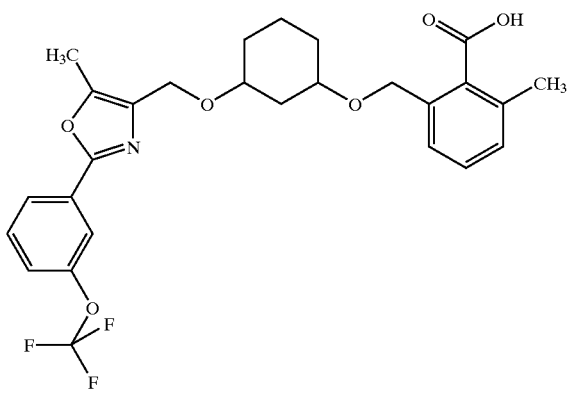

64

2-{3-[2-(3-Trifluoromethoxyphenyl)-5-methyloxazol-4-ylmethoxy]cyclohexyloxymethyl}-6-methylbenzoic Acid 64

Using methyl 2-(3-hydroxycyclohexyloxymethyl)-6-methylbenzoate and 2-(3-trifluoromethoxyphenyl)-4-iodomethyl-5-methyloxazole as starting materials in the procedure of Example XXXI, gave the product 64 of molecular weight 519.52 ($C_{27}H_{28}F_3NO_6$), MS(ESI): 520.20 (M+H$^+$).

EXAMPLE XLIII

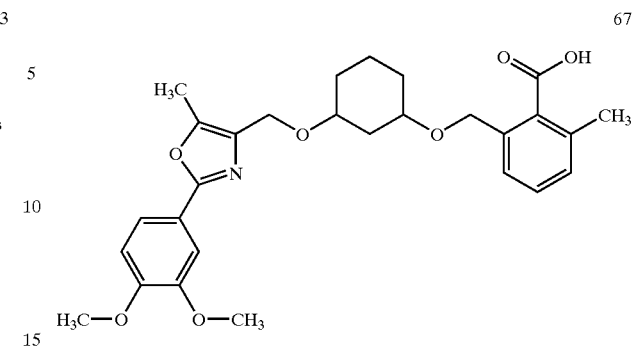

2-{3-[2-(3,4-Dimethoxyphenyl)-5-methyloxazol-4-ylmethoxy]cyclohexyloxymethyl}-6-methylbenzoic Acid 67

Using methyl 2-(3-hydroxycyclohexyloxymethyl)-6-methylbenzoate and 2-(3,4-dimethoxyphenyl)4-iodomethyl-5-methyloxazol as starting materials in the procedure of Example XXXI, gave the product 67 of molecular weight 495.58 ($C_{28}H_{33}NO7$), MS(ESI): 496.20 (M+H$^+$).

EXAMPLE XLIV

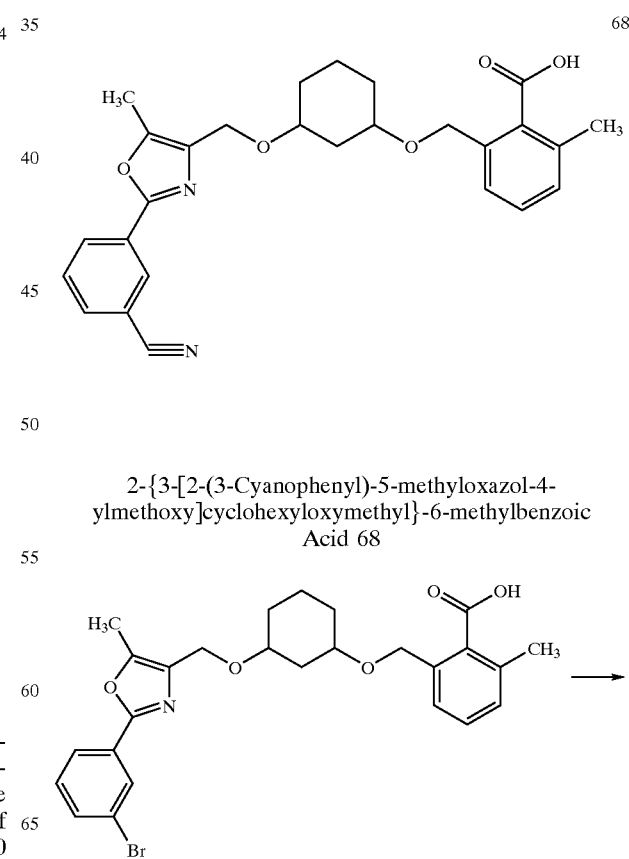

2-{3-[2-(3-Cyanophenyl)-5-methyloxazol-4-ylmethoxy]cyclohexyloxymethyl}-6-methylbenzoic Acid 68

-continued

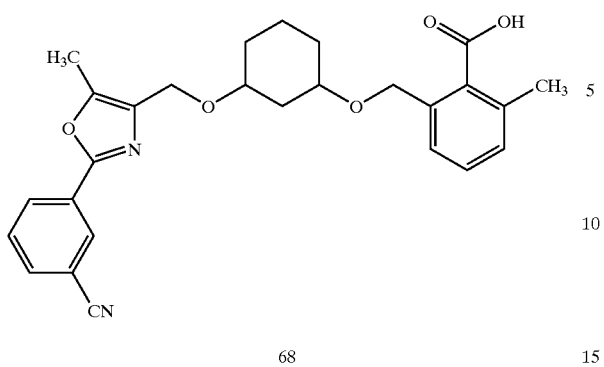

68

13 mg of 2-{3-[2-(3-bromophenyl)-5-methyloxazol-4-ylmethoxy]cyclohexyloxymethyl}-6-methylbenzoic acid and 25 mg of zinc cyanide were dissolved in 5 ml of dimethylformamide. The reaction mixture was degassed and charged with argon, and 20 mg of tetrakistriphenylphosphinepalladium were added. The mixture was stirred at 100° C. for 12 hours. After cooling to room temperature, water was added to the reaction mixture, which was then extracted with ethyl acetate. The combined organic phases were dried over magnesium sulfate, the solvents were removed under reduced pressure and the residue was purified by RP-HPLC. This gave 68 as an amorphous light-yellow solid. $C_{27}H_{28}N_2O_5$ (460.53), MS(ESI): 461.20 (M+H$^+$).

EXAMPLE XLV

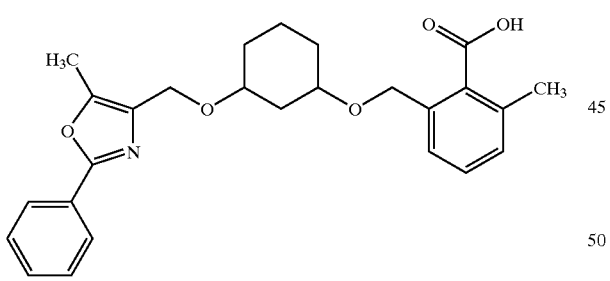

69

2-Methyl-6-[3-(5-methyl-2-phenyloxazol-4-ylmethoxy)cyclohexyloxymethyl]benzoic Acid 69

Using methyl 2-(3-hydroxycyclohexyloxymethyl)-6-methylbenzoate and 2-phenyl-4-iodomethyl-5-methyloxazole as starting materials in the procedure of Example XXXI, gave the product 69 of molecular weight 435.52 ($C_{26}H_{29}NO_5$), MS(ESI): 436.32 (M+H$^+$).

EXAMPLE XLVI

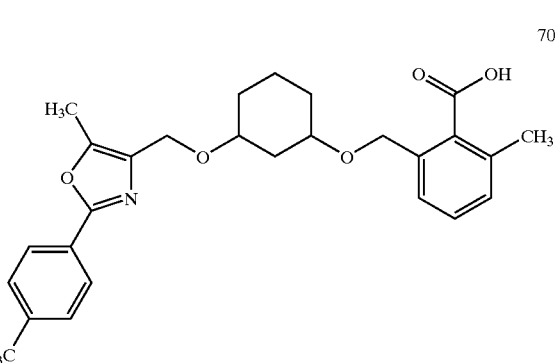

70

2-Methyl-6-[3-(5-methyl-2-p-tolyloxazol-4-ylmethoxyscyclohexyloxyme thyl]benzoic Acid 70

Using methyl 2-(3-hydroxycyclohexyloxymethyl)-6-methylbenzoate and 2-(4-methylphenyl)-4-iodomethyl-5-methyloxazole as starting materials in the procedure of Example XXXI, gave the product 70 of molecular weight 449.55 ($C_{27}H_{31}NO_5$), MS(ESI): 450.36 (M+H$^+$).

EXAMPLE XLVII

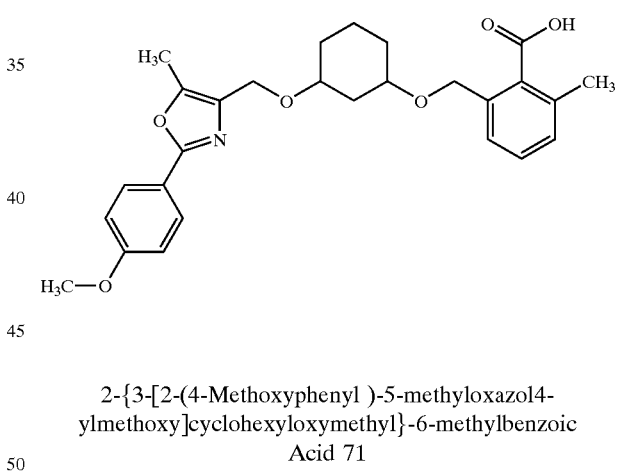

71

2-{3-[2-(4-Methoxyphenyl)-5-methyloxazol4-ylmethoxy]cyclohexyloxymethyl}-6-methylbenzoic Acid 71

Using methyl 2-(3-hydroxycyclohexyloxymethyl)-6-methylbenzoate and 2-(4-methoxyphenyl)-4-iodomethyl-5-methyloxazole as starting materials in the procedure of Example XXXI, gave the product 71 of molecular weight 465.55 ($C_{27}H_{31}NO_6$), MS(ESI): 466.37 (M+H$^+$).

While the invention has been described in connection with certain preferred embodiments so that aspects thereof may be more fully understood and appreciated, it is not intended to limit the invention to these particular embodiments. On the contrary, it is intended to cover all alternatives, modifications and equivalents as may be included within the scope of the invention as defined by the appended claims.

What is claimed is:

1. A compound of formula I

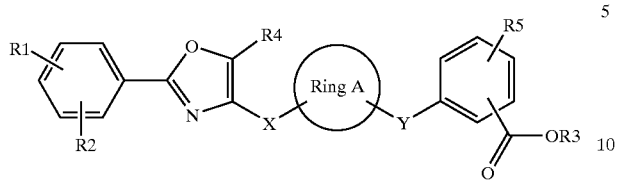

in which

Ring A is $(C_3-C_8)$-cycloalkyl or $(C_3-C_8)$-cycloalkenyl where, in the cycloalkyl or cycloalkenyl rings, one or more carbon atoms may be replaced by oxygen atoms;

R1, R2, R4, R5 independently of one another are H, F, Cl, Br, OH, $NO_2$, $CF_3$, $OCF_3$, $(C_1-C_6)$-alkyl or O-$(C_1-C_6)$-alkyl;

R3 is H or $(C_1-C_6)$-alkyl;

X is $(C_1-C_6)$-alkyl where, in the alkyl group, one or more carbon atoms may be replaced by oxygen atoms;

Y is $(C_1-C6)$-alkyl where, in the alkyl group, one or more carbon atoms may be replaced by oxygen atoms;

and its physiologically acceptable salts.

2. The compound of claim 1 and its physiologically acceptable salts, wherein R5 is $(C_1-C_6)$-alkyl.

3. The compound of claim 1 and its physiologically acceptable salts, wherein Ring A is $(C_3-C_8)$-cycloalkyl or $(C_3-C_8)$-cycloalkenyl.

4. A compound of formula Ia

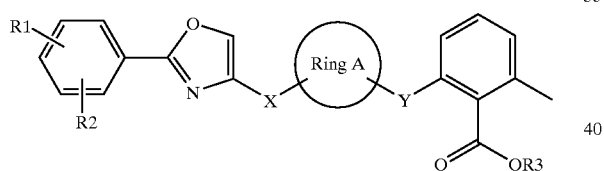

wherein

Ring A is cyclohexyl;

R1, R2 independently of one another are H,. F, Cl, Br, OH, $NO_2$, $CF_3$, $OCF_3$, $(C_1-C_6)$-alkyl or O-$(C_1-C_6)$-alkyl;

R3 is H or $(C_1-C_6)$-alkyl;

X is $(C_1-C_6)$-alkyl where, in the alkyl group, one or more carbon atoms may be replaced by oxygen atoms;

Y is $(C_1-C_6)$-alkyl where, in the alkyl group, one or more carbon atoms may be replaced by oxygen atoms;

and its physiologically acceptable salts.

5. A pharmaceutical, comprising:
   at least one compound or physiologically acceptable salt of claim 1; and
   a pharmaceutically acceptable carrier.

6. A pharmaceutical, comprising:
   at least one compound or physiologically acceptable salt of claim 1;
   at least one further active compound; and
   a pharmaceutically acceptable carrier.

7. A pharmaceutical, comprising:
   at least one compound or physiologically acceptable salt of claim 1;
   at least one lipid- or triglyceride-lowering active compound; and
   a pharmaceutically acceptable carrier.

8. A method of treating a lipid metabolism disorder, comprising:
   administering to a host in need of such treatment an effective amount of at least one compound or physiologically acceptable salt of claim 1 or claim 4.

9. A method of treating type II diabetes, comprising:
   administering to a host in need of such treatment an effective amount of at least one compound or physiologically acceptable salt of claim 1 or claim 4.

10. A method of treating syndrome X, comprising:
    administering to a host in need of such treatment an effective amount of at least one compound or physiologically acceptable salt of claim 1 or claim 4.

11. A method of treating disturbed glucose tolerance, comprising:
    administering to a host in need of such treatment an effective amount of at least one compound or physiologically acceptable salt of claim 1 or claim 4.

12. A method of treating eating disorders, comprising:
    administering to a host in need of such treatment an effective amount of at least one compound or physiologically acceptable salt of claim 1 or claim 4.

13. A method of treating obesity, comprising:
    administering to a host in need of such treatment an effective amount of at least one compound or physiologically acceptable salt of claim 1 or claim 4.

14. A method of treating cardiomyopathy, comprising:
    administering to a host in need of such treatment an effective amount of at least one compound or physiologically acceptable salt of claim 1 or claim 4.

15. A method of treating cardiac insufficiency, comprising:
    administering to a host in need of such treatment an effective amount of at least one compound or physiologically acceptable salt of claim 1 or claim 4.

16. A method of treating osteoporosis, comprising:
    administering to a host in need of such treatment an effective amount of at least one compound or physiologically acceptable salt of claim 1 or claim 4.

17. A method of treating atherosclerosis, comprising:
    administering to a host in need of such treatment an effective amount of at least one compound or physiologically acceptable salt of claim 1 or claim 4.

18. A method of treating Alzheimer's disease, comprising:
    administering to a host in need of such treatment an effective amount of at least one compound or physiologically acceptable salt of claim 1 or claim 4.

19. A method of treating inflammation, comprising:
    administering to a host in need of such treatment an effective amount of at least one compound or physiologically acceptable salt of claim 1 or claim 4.

20. The method of treating a lipid metabolism disorder of claim 8, further comprising administering to a host in need of such treatment an effective amount of at least one further active compound.

21. The method of treating type II diabetes of claim 9, further comprising administering to a host in need of such treatment an effective amount of at least one further active compound.

22. The method of treating syndrome X of claim 10, further comprising administering to a host in need of such treatment an effective amount of at least one further active compound.

23. A process for preparing a pharmaceutical, comprising:

mixing at least one compound or physiologically acceptable salt of claim 1 with a pharmaceutically acceptable carrier to form a mixture; and bringing this mixture into a form suitable for administration to form the pharmaceutical.

* * * * *

UNITED STATES PATENT AND TRADEMARK OFFICE
CERTIFICATE OF CORRECTION

PATENT NO. : 6,624,185 B2
DATED : September 23, 2003
INVENTOR(S) : Glombik et al.

It is certified that error appears in the above-identified patent and that said Letters Patent is hereby corrected as shown below:

Column 49,
Line 24, "($C_1$-C6)-alkyl" should read -- ($C_1$-$C_6$)-alkyl --
Line 46, "H,.F," should read -- H, F, --

Signed and Sealed this

Thirtieth Day of December, 2003

JAMES E. ROGAN
*Director of the United States Patent and Trademark Office*